(12) United States Patent
Stroock et al.

(10) Patent No.: US 11,536,660 B2
(45) Date of Patent: Dec. 27, 2022

(54) IN SITU SENSING OF WATER POTENTIAL

(71) Applicant: CORNELL UNIVERSITY, Ithaca, NY (US)

(72) Inventors: Abraham Stroock, Ithaca, NY (US); Michael Gore, Ithaca, NY (US); Duke Pauli, Ithaca, NY (US); Olivier Vincent, Biviers (FR); Piyush Jain, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 372 days.

(21) Appl. No.: 16/634,665

(22) PCT Filed: Jul. 30, 2018

(86) PCT No.: PCT/US2018/044428
§ 371 (c)(1),
(2) Date: Jan. 28, 2020

(87) PCT Pub. No.: WO2019/023712
PCT Pub. Date: Jan. 31, 2019

(65) Prior Publication Data
US 2021/0116374 A1    Apr. 22, 2021

Related U.S. Application Data

(60) Provisional application No. 62/538,308, filed on Jul. 28, 2017.

(51) Int. Cl.
*C09K 11/06* (2006.01)
*C09K 11/02* (2006.01)
(Continued)

(52) U.S. Cl.
CPC ......... *G01N 21/6428* (2013.01); *C09K 11/02* (2013.01); *C09K 11/06* (2013.01);
(Continued)

(58) Field of Classification Search
CPC ......... B82Y 15/00; B82Y 20/00; B82Y 40/00; C09K 11/02; C09K 11/06; G01N 21/6428;
(Continued)

(56) References Cited

U.S. PATENT DOCUMENTS 6,597,991 B1    7/2003    Meron. et al.
8,129,111 B2 *  3/2012    Tang ............... C09B 69/008
                                                    435/7.1
(Continued)

FOREIGN PATENT DOCUMENTS

EP    3135102 A1    3/2017
WO    2004/112467 A1    6/2004
(Continued)

OTHER PUBLICATIONS

International Search Report and Written Opinion for corresponding Application No. PCT/US2018/044428 (dated Dec. 3, 2018).

*Primary Examiner* — Mark R Gaworecki
(74) *Attorney, Agent, or Firm* — Troutman Pepper Hamilton Sanders LLP (Rochester)

(57) ABSTRACT

The present invention relates to a method for in situ sensing of water stress in a plant by contacting a plant with a biosensor, where the biosensor comprises a material capable of giving a detectable response to changes in local water potential in the plant and detecting the detectable response thereby sensing water stress in the plant. The invention further relates to a method for determining water potential in a substance, a biosensor, a system for determining water potential in a substance, a method for determining water potential in a substance, a water potential measurement computing device, and a non-transitory computer readable medium having stored thereon instructions for determining water potential in a substance.

20 Claims, 17 Drawing Sheets

(51) Int. Cl.
  *G01N 21/64* (2006.01)
  *G01N 33/00* (2006.01)
  *B82Y 15/00* (2011.01)
  *B82Y 20/00* (2011.01)
  *B82Y 40/00* (2011.01)

(52) U.S. Cl.
  CPC .......... *G01N 33/0098* (2013.01); *B82Y 15/00* (2013.01); *B82Y 20/00* (2013.01); *B82Y 40/00* (2013.01); *G01N 2021/6432* (2013.01); *G01N 2021/6439* (2013.01); *G01N 2201/0631* (2013.01); *G01N 2201/08* (2013.01)

(58) Field of Classification Search
  CPC ............... G01N 21/81; G01N 33/0098; G01N 2021/4742; G01N 2021/6432; G01N 2021/6439; G01N 2021/7723; G01N 2021/773; G01N 2021/7786; G01N 2021/8466; G01N 2201/0631; G01N 2201/80
  See application file for complete search history.

(56) References Cited

U.S. PATENT DOCUMENTS

| | | | |
|---|---|---|---|
| 8,590,373 B1 | 11/2013 | Van Bavel | |
| 8,695,407 B2 | 4/2014 | Stroock et al. | |
| 8,806,942 B2 | 8/2014 | Kegeyama | |
| 9,451,745 B1 | 9/2016 | O'Shaughnessy et al. | |
| 9,688,743 B2 | 6/2017 | Schmidt et al. | |
| 2005/0072935 A1 | 4/2005 | Lussier | |
| 2007/0249063 A1* | 10/2007 | Deshong | G01N 33/54326 435/6.12 |
| 2008/0220407 A1* | 9/2008 | Tang | G01N 21/6428 562/42 |
| 2010/0009362 A1* | 1/2010 | Tang | C09B 23/0075 435/6.12 |
| 2012/0100631 A1* | 4/2012 | Dillmore | G01N 33/92 436/501 |
| 2014/0326801 A1 | 11/2014 | Upadhyaya et al. | |
| 2015/0027040 A1 | 1/2015 | Redden | |
| 2015/0203864 A1 | 7/2015 | Rothstein et al. | |
| 2016/0327536 A1 | 11/2016 | Meron | |
| 2017/0032258 A1 | 2/2017 | Miresmailli et al. | |
| 2018/0003668 A1 | 1/2018 | Li et al. | |
| 2018/0146632 A1 | 5/2018 | Meron | |
| 2022/0003676 A1* | 1/2022 | Mazed | G01N 33/54366 |

FOREIGN PATENT DOCUMENTS

| | | |
|---|---|---|
| WO | 2010/121176 A2 | 10/2010 |
| WO | 2016/168585 A1 | 10/2016 |
| WO | 2016/185477 A1 | 11/2016 |
| WO | 2017/096317 A1 | 6/2017 |

* cited by examiner

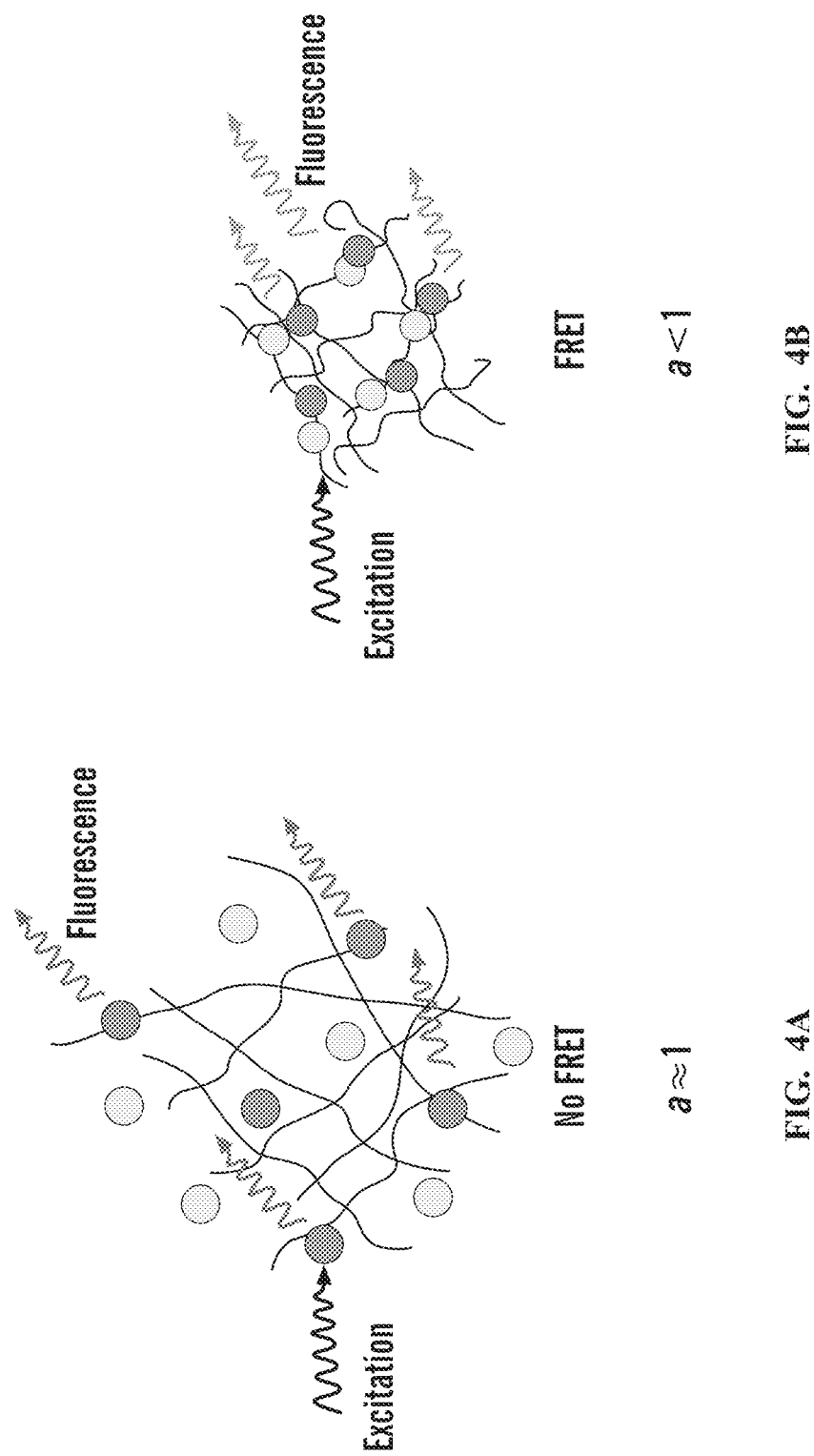

IN SITU SENSING OF WATER POTENTIAL

This application is a national stage application under 35 U.S.C. § 371 of PCT Application No. PCT/US2018/044428, filed Jul. 30, 2018, which claims the priority benefit of U.S. Provisional Patent Application Ser. No. 62/538,308 filed Jul. 28, 2017, which is hereby incorporated by reference in its entirety.

FIELD OF THE INVENTION

The present invention relates generally to biosensors and systems for determining water potential in a substance, for example for in situ sensing of water stress in plants, and for high-throughput phenotyping.

BACKGROUND OF THE INVENTION

Changing climatic conditions pose numerous threats to humanity but none as severe as food insecurity. *World Food Situation*, Food and Agriculture Organization of the United Nations, FAO Cereal Supply and Demand Brief (2015). The increased frequency and severity of drought and high temperature conditions makes it imperative to develop crop plants that are able to cope with these environmental challenges in a sustainable manner. Sinclair T. R., HANDBOOK OF CLIMATE CHANGE AND AGROECOSYSTEMS: IMPACTS, ADAPTATION, AND MITIGATION, eds. D. Hillel & C. Rosenzweig, Imperial College Press (2010). In order to develop plants with effective water use (EWU) as well as to understand the physiological and genetic basis of abiotic stress tolerance, the ability to screen the response of large plant populations to stress is needed. Relative to the rapid evolution of genotyping technologies, the development of phenotyping tools for complex traits has lagged, hampering the study of key stress-adaptive traits and leading to an extensive knowledge gap. Richards et al., "Breeding for Improved Water Productivity in Temperate Cereals: Phenotyping, Quantitative Trait Loci, Markers and the Selection Environment," *Functional Plant Biology* 37:85-97 (2010). Leaf water potential ($\Psi_{leaf}$) represents the best single indicator of plant water status, because it integrates environmental conditions (e.g., water availability and evaporative demand) and plant responses (e.g., stomatal regulation). Nobel P. S., PHYSICOCHEMICAL AND ENVIRONMENTAL PLANT PHYSIOLOGY. 2nd ed., Academic Press (1999). To date, techniques for the measurement of $\Psi_{leaf}$ have been too cumbersome and expensive to be exploited in high throughput phenotyping strategies.

Breeding and Phenotyping Strategies for EWU. Traditional breeding approaches that focus on selecting for yield within drought-prone or variable environments suffer from strong genotype-by-environment interactions (GxE) that inhibit the selection of superior genotypes and the potential for identifying useful genetic markers. Richards R. A., "Physiological Traits Used in the Breeding of New Cultivars for Water-Scarce Environments," *Agricultural Water Management* 1:197-211 (2006). This realization has motivated efforts to identify physiological traits that control EWU as well as methods to measure them in a high-throughput manner. While there exist important examples of success (e.g., based on axial xylem resistance in wheat and anthesis-silking interval in maize), the gains in yield have been modest and the generality of these traits as useful indicators of EWU across species and environments remains unclear. Richards R. A., "Physiological Traits Used in the Breeding of New Cultivars for Water-Scarce Environments," *Agricultural Water Management* 1:197-211 (2006). More recently, measurements of root structure have been pursued, but tend to require significant manual intervention for field-grown plants and have yet to provide significant improvements in EWU. Van Oosterom et al., "Hybrid Variation for Root System Efficiency in Maize: Potential Links to Drought Adaptation," *Functional Plant Biology* 43:502-511 (2016); Tuberosa R., "Phenotyping for Drought Tolerance of Crops in the Genomics Era," *Frontiers in Physiology* 3:347 (2012). Investigators have considered traits more directly related to water relations, for example, limited transpiration, but predict that strong GxE effects would need to be accounted for. Messina et al., "Limited-Transpiration Trait May Increase Maize Drought Tolerance in the US Corn Belt," *Agronomy Journal* 107:1978-1986 (2015). Farquhar's and Richards' phenotyping methods based on using carbon isotope discrimination as a surrogate for water use efficiency stands out for its relative generality and ease of implementation. Farquhar et al., "Isotopic Composition of Plant Carbon Correlates with Water-Use Efficiency of Wheat Genotypes," *Functional Plant Biology* 11:539-552 (1984). Nonetheless, isotope discrimination remains impractical for implementation on large mapping populations and can suffer from significant GxE effects. Richards R. A., "Physiological Traits Used in the Breeding of New Cultivars for Water-Scarce Environments," *Agricultural Water Management* 1:197-211 (2006); Cordon et al., "Carbon Isotope Discrimination is Positively Correlated with Grain Yield and Dry Matter Production in Field-Grown Wheat," *Crop Science* 27:996-1001 (1987). Continued progress in the development of water efficient crops for a changing climate will depend on new methods to define physiological traits associated with EWU.

Plant biosensors. While enormous progress has been made over the past decades in the development of sensing technologies for human physiology, no commensurate evolution has occurred for plants. As such, most phenotyping strategies based on physiological traits depend on the measurement of macroscopic features such as plant, leaf, and root size and architecture based on direct observation or imaging techniques. Tuberosa R., "Phenotyping for Drought Tolerance of Crops in the Genomics Era," *Frontiers in Physiology* 3:347 (2012). Measurements of finer-scale structural and dynamic traits currently requires frequent destructive sampling and manual measurements (e.g., via microscopy). Emerging approaches with genetically encoded biosensors for in situ measurements present attractive possibilities for phenotyping, but remain challenging to implement and have yet to address EWU. Palmer et al., "Design and Application of Genetically Encoded Biosensors," *Trends in Biotechnology* 29:144-152 (2011). The use of nanomaterials for sensing on cellular and whole organism scales has progressed rapidly in mammalian contexts, (Lee et al., "Nanoparticle PEBBLE Sensors in Live Cells and in Vivo," *Annual Review of Analytical Chemistry* 2:57-76 (2009); Park et al., "Biodegradable Luminescent Porous Silicon Nanoparticles for in Vivo Applications," *Nat. Mater.* 8:331-336 (2009); Lin et al., "A Porous Silicon-Based Optical Interferometric Biosensor," *Science* 278:840-843 (1997)), but analogous approaches have not been developed to address the specific biological and technological challenges presented by plants and agriculture.

The present invention unites expertise in materials engineering, plant breeding, genetics, high-throughput phenotyping, water relations, and crop modeling to address the above challenges and overcome these and other deficiencies in the art.

SUMMARY OF THE INVENTION

A first aspect of the present invention relates to a method for determining water potential in a substance. The method comprises contacting a substance with a biosensor (e.g., a non-toxic, biodegradable biosensor), where the biosensor comprises a material capable of giving a detectable response to changes in local water potential, and detecting the detectable response thereby determining water potential in the substance.

A second aspect of the present invention relates to a method for in situ sensing of water stress in a plant. The method comprises contacting a plant with a biosensor, where the biosensor comprises a material capable of giving a detectable response to changes in local water potential in the plant, and detecting the detectable response thereby sensing water stress in the plant.

A third aspect of the present invention relates to a biosensor. The biosensor comprises a hydrophilic polymer matrix formed by polymerization of a first monomer, a second monomer, and a third monomer, and the matrix is conjugated with a pair of donor and acceptor fluorophores that exhibit Fluorescence Resonance Energy Transfer.

A fourth aspect of the present invention relates to a system for determining water potential in a substance. The system comprises an illumination source configured to provide illumination at an excitation wavelength to a substance contacted with a non-toxic, biodegradable biosensor comprising a material capable of giving a detectable response to changes in local water potential; a spectrometer configured to receive reflected illumination from the substance and determine an emission spectra based on the detectable response from the material of the biosensor, wherein the spectrometer comprises a hyperspectral imaging device; and a water potential measurement computing device, comprising a processor and a memory coupled to the processor which is configured to execute one or more programmed instructions comprising and stored in the memory to: receive the emission spectra from the spectrometer; receive the emission spectra from the hyperspectral imaging device; and determine a water potential of the substance based on the received emission spectra.

A fifth aspect of the present invention relates to a method for determining water potential in a substance. The method comprises receiving, by a water potential measurement computing device, an emission spectra from a spectrometer based on a detectable response from a substance contacted with a non-toxic, biodegradable biosensor comprising a material capable of giving the detectable response to changes in local water potential when the substance is illuminated at an excitation wavelength; and determining, by the water potential measurement computing device, a water potential of the substance based on the received emission spectra from the spectrometer.

A sixth aspect of the present invention relates to a water potential measurement computing device. The computing device comprises a processor and a memory coupled to the processor which is configured to execute one or more programmed instructions comprising and stored in the memory to: receive an emission spectrum from a spectrometer based on a detectable response from a substance contacted with a non-toxic, biodegradable biosensor comprising a material capable of giving the detectable response to changes in local water potential when the substance is illuminated at an excitation wavelength; and determine a water potential of the substance based on the received emission spectra from the spectrometer.

A seventh aspect of the present invention relates to a non-transitory computer readable medium having stored thereon instructions for determining water potential in a substance. The non-transitory computer readable medium comprises executable code which when executed by a processor, causes the processor to perform steps comprising: receiving an emission spectra from a spectrometer based on a detectable response from a substance contacted with a non-toxic, biodegradable biosensor comprising a material capable of giving the detectable response to changes in local water potential when the substance is illuminated at an excitation wavelength; and determining a water potential of the substance based on the received emission spectra from the spectrometer.

Leaf water potential ($\Psi_{leaf}$) represents the best single indicator of plant water status because it integrates environmental conditions (e.g., water availability and evaporative demand) and genotype specific plant responses (e.g., stomatal regulation and anatomy). The lack of high-throughput phenotyping methods to measure $\Psi_{leaf}$ on an individual basis poses a significant challenge to decoupling the environment and genotype contributions in the assessment of effective water use (EWU) in plants. The present invention presents steps toward the development of a dispersible biosensor of water potential that will allow for remote measurement of $\Psi_{leaf}$ at the level of individual plants. The present invention considers 1) the characterization of delivery of biosensors to the leaf tissue in maize, 2) optical characterization of embedded biosensors, and 3) design considerations for materials that respond optically to changes in water potential. Also discovered are opportunities to define new traits that capture EWU and their use within a phenotyping framework to access the associated quantitative trait loci. Here, the EWU is considered the maximization of the productive use of available soil water. Blum A., "Effective Use of Water (EUW) and Not Water-Use Efficiency (WUE) is the Target of Crop Yield Improvement Under Drought Stress," *Field Crops Research* 112: 119-123 (2009), which is hereby incorporated by reference in its entirety.

It is hypothesized that the ability to measure $\Psi_{leaf}$ within an integrated, high throughput phenotyping strategy will allow for the discovery and quantification of new traits that define EWU in important crops (maize and wheat) and lead to the identification of genetic loci that control them. To test this hypothesis, synthetic microparticulate biosensors (referred to as hydrophilic polymer matrix, "AquaDust" or "aquaDust" herein) were developed that can be embedded in the mesophyll to provide optical signals that respond to $\Psi_{leaf}$. Further, new phenotyping strategies are built for EWU based on this new capability, conventional measurement tools, and crop models.

The present invention brings a new approach to the challenge of phenotyping in particular and to the need for new tools to study plant physiology in general. The nanomaterial-based strategy has not been previously explored in plant biology. Furthermore, the particular target application in the present invention overcomes important technical challenges: no dispersible biosensor of water potential has been previously reported in any context, and methods for the delivery and interrogation of such biosensors in plants have never been previously explored. Additionally, identifying and quantifying new traits that affect EWU within a high-throughput approach implicates complex biophysical processes and requires the development of innovative approaches that integrate advanced instrumentation, crop modeling, and genetic analysis. Taken together, these characteristics imply a level of uncertainty about approaches and outcomes that make it unsuitable for standard programmatic review. The present invention addresses these challenges and uncertainties. The present invention is unexpected and transformative: the development of in planta biosensors capable of capturing the internal dynamics of water potential will have high impact by opening a powerful new route to study plant water relations in both fundamental and applied contexts. When coupled with ecophysiological models, this tool will help elucidate the physiology controlling plant-water relations and the critical balance between $CO_2$ uptake and water loss due to transpiration. When coupled with additional measurements of plant and environmental parameters and genetic analysis across diverse plant populations, this tool will be transformative in breeding crops that have the capacity to tightly regulate response to the environment without adversely affecting yield potential. Finally, the present invention serves as a template for future collaborations in which materials engineering addresses pressing problems in plant science and agriculture.

BRIEF DESCRIPTION OF THE DRAWINGS

FIG. 1A is a diagram showing aquaDust (shaded in dark gray) deployed in mesophyll such that leaf water potential ($\Psi_{leaf}$) can be sensed via calibrated reflectivity or fluorescence. FIG. 1B shows porous silicon-based aquaDust with strong, tunable dependence of reflectance on water potential (vapor activity). FIG. 1C shows the proposed mechanism of hydrogel-based fluorescent aquaDust based on the relationship of FRET with water potential via hydration state of gel. FIG. 1D measures EWU phenotypes based on multi-parameter envirotyping which can be integrated using crop growth models for genetic mapping of EWU to identify causal genes (µTensiometer is a Cornell technology). Pagay et al., "A Microtensiometer Capable of Measuring Water Potentials Below –10 MPa," Lab on a Chip 14:2806-2817 (2014), which is hereby incorporated by reference in its entirety. The leaf clamp provides direct, spectroscopic measurements of aquaDust and chlorophyll fluorescence. UAV-mounted imaging provides proximal measurements.

FIGS. 4A-4B illustrates a sketch of FRET response with fluorophore dye (dark gray and light gray dots) incorporated in the polymer matrix with change in vapor activity α.

FIG. 6A shows a schematic of one nanoparticle (one 'aquaDust'): swollen, 'relaxed' state when water potential, $\Psi$, =0, i.e., no stress condition result in low FRET between donor (shown in light gray circles) and acceptor (shown in dark gray circles) dye; and collapsed state when water potential, $\Psi|0$, i.e., stressed condition result in high FRET between fluorophores, thereby, altering the emission spectra. FIG. 6B illustrates size distribution with respect to intensity of scattering in dynamic light scattering measurement, with respect to the number of particles and with respect to the volume of particles. FIG. 6C shows chemical composition for gel matrix of aquaDust: acrylamide polymer chain is interspersed with N-3 Aminopropyl methacrylamide (APMA) which is conjugated to donor and acceptor fluorophores, shown in light gray (Oregon Green) and dark gray (Rhodamine) circles. In FIG. 6D, aquaDust solution is infiltrated in leaf using pressure injection of solution by clamping on the leaf. Cross-section illustration shows aquaDust lines up the intercellular air spaces and apoplastic surfaces of mesophyll and bundle sheath cells. In FIG. 6E, typical infiltration in maize leaf is evident with darkening of infiltrated zone (Scale bar: 1 cm); cross-section of un-infiltrated and infiltrated zone is imaged under confocal microscope where the increase in fluorescence in channel is attributed to aquaDust (Scale bar: 50 µm). FIG. 6F is a schematic which shows instrumentation for a typical in-situ measurement. Mercury lamp light source is used as source for illumination, a narrow-band wavelength optical filter is used to select the excitation light wavelength (here, it is 470-500 nm) and is used to excite aquaDust using a reflection probe where six optical fibers are used for illumination. The reflected light is captured by the central fiber and sent to spectrometer after filtering out the reflected excitation wavelengths, to avoid the saturation of detector, using an emission filter. The spectrometer is connected to a laptop for recording and saving the spectra.

FIG. 7A presents spectra of AquaDust with different water potential as measured with a pressure chamber. Bold lines represent spectra that are closest to the mean FRET Efficiency obtained for a given water potential. The translucent band represents the error in the spectra as obtained from multiple measurements. FIG. 7B shows FRET Efficiency as calculated from the spectra in FIG. 7A plotted against water potential (intensity or concentration effects were not considered). Theoretical prediction as obtained from Flory-Rehner theory and Dipole-Plane FRET model is plotted against water potential measured from the pressure chamber. FIG. 7C shows FRET Efficiency plotted as a function of distance from spot of infiltration (maximum distance affected by the damage due to infiltration 7 mm). In FIG. 7D, response time of aquaDust is measured by placing cut-out maize leaf with exposed region in water pouch and pressuring it at +2 bars in a pressure chamber, water potential from aquaDust is plotted against time after it was pressurized.

DETAILED DESCRIPTION OF THE INVENTION

One aspect of the present invention relates to a method for determining water potential in a substance. The method comprises contacting a substance with a biosensor, where the biosensor comprises a material capable of giving a detectable response to changes in local water potential and detecting the detectable response thereby determining water potential in the sub stance.

Water potential ($\Psi$) is a form of chemical potential of water. It is the most widely measured plant water status parameter and is a useful indicator to predict plant and fruit growth, yield, and fruit composition and quality. One advantage of using water potential to quantify plant water status is that at equilibrium, both liquid and vapor (gas) phases have identical values of water potential.

Plant water relations are governed by chemical (e.g., water) potential and its gradients, not by water content. There have been many studies of the effects of water stress on plant productivity and product quality though these have not always led to predictive tools. The main problem is that in-water status is very dynamic, both daily and seasonally, as plant water stress responds to both soil moisture and atmospheric evaporative demand. Ideal measures must be direct measurement of chemical potential, continuous to capture the dynamics, and inexpensive enough to allow spatial resolution.

There is a range of environmental factors in which the plant can grow under the best condition from a physiological viewpoint, depending on species of plants. Beyond the range of environmental factors, the growth of plants is hindered, the yield of plants is decreased, and the plant is disordered and blighted. A symptomatic state in which with the foregoing unsuitable environmental factor, the plant is physiologically inactive is referred to as environmental stress, and water stress, temperature stress, salt stress and the like are listed as the environmental stress. In the plant having the vascular tissue, the xylem serves as the transport route of water, and with a negative pressure generated by the transpiration in the daytime, water is pulled up to the leafs from the roots. When water stress, the salt stress, the growth difficulty of the root and the like disturbs the supply of water, the negative pressure of the xylem is increased, and the state in which the negative pressure is increased is referred to as the state in which water stress is increased.

Figure 1B:
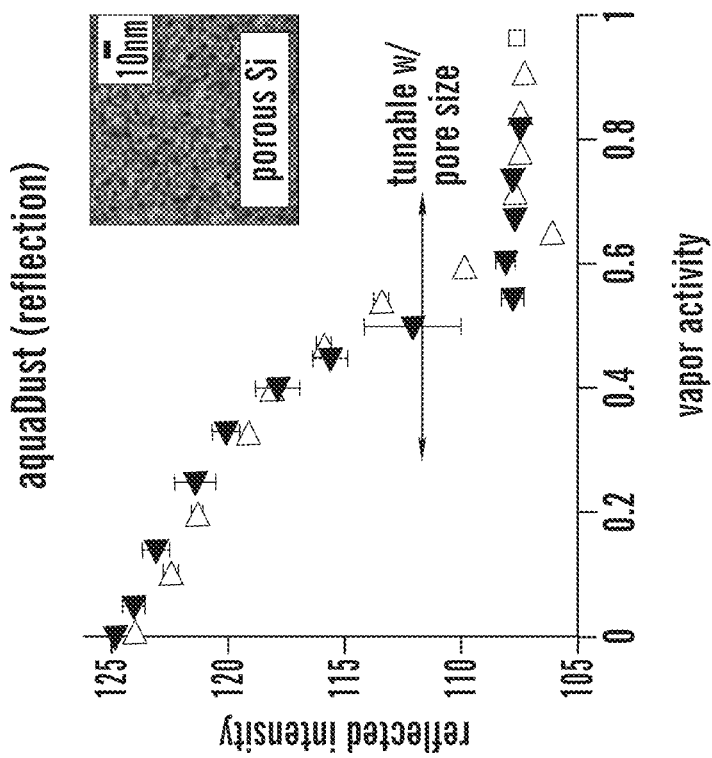
FIGS. 1A-1D depict aquaDust-enabled high-throughput phenotyping for Effective Water Use (EWU).
Figure 1A:
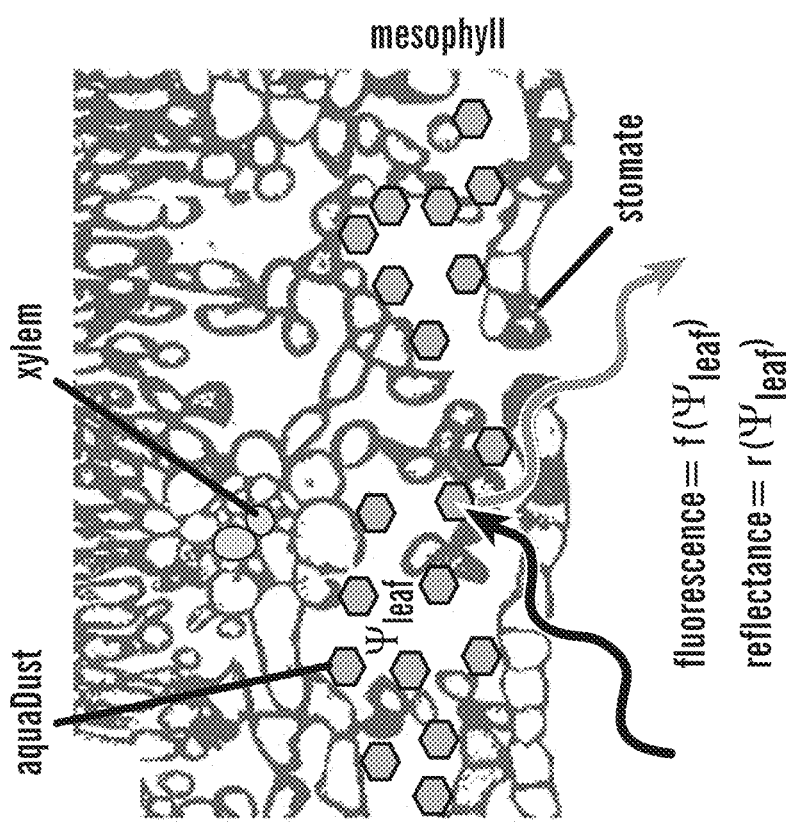
Figures 1C, 1D:
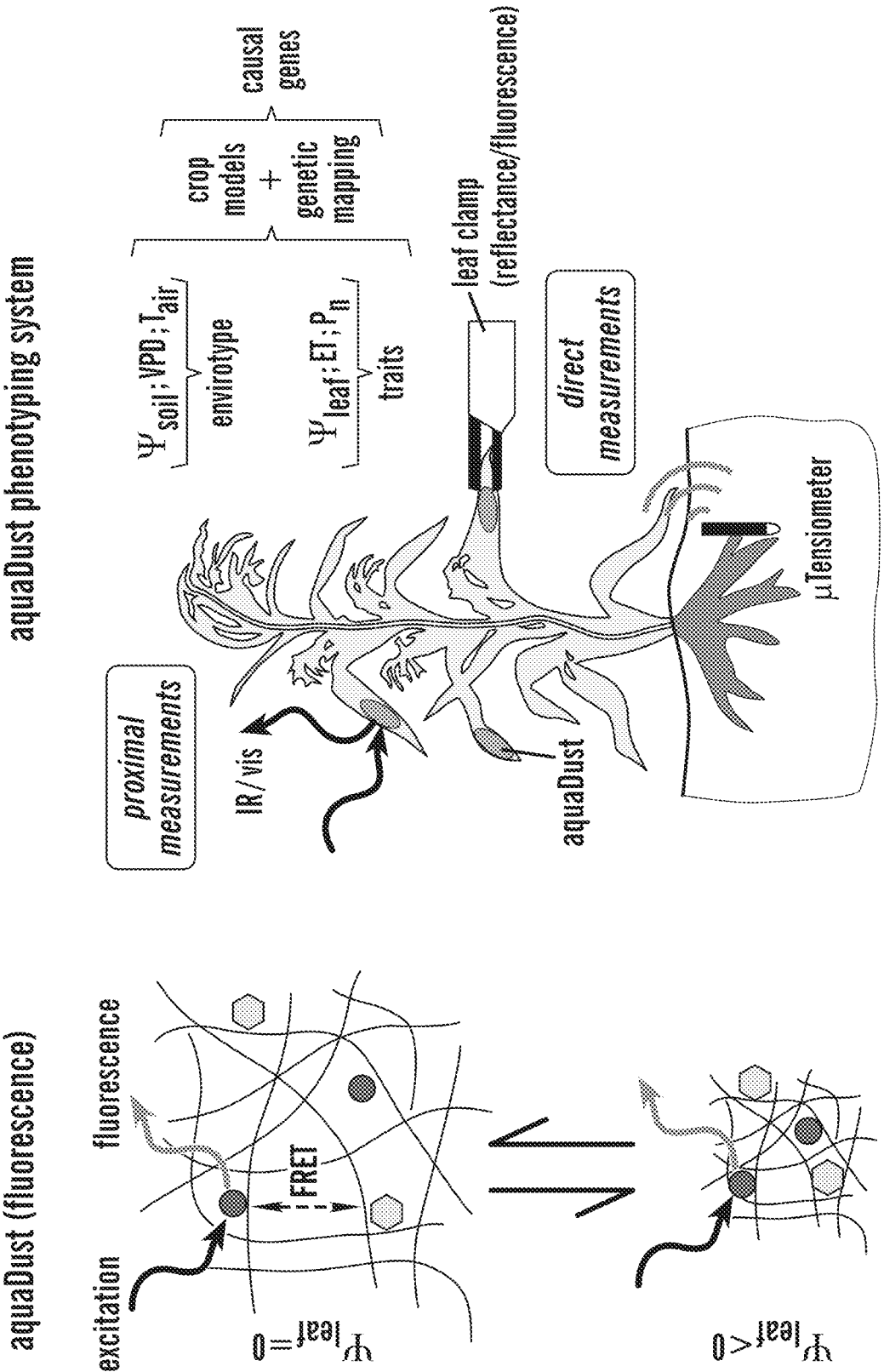
Figure 2:
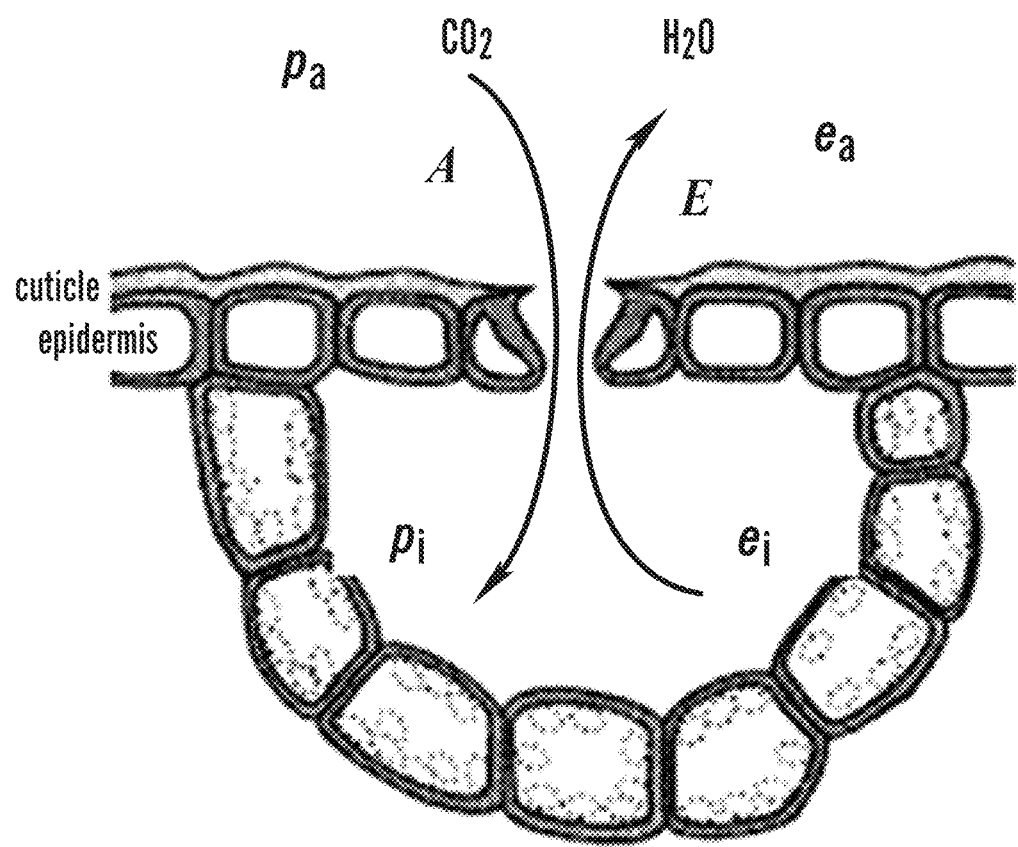
FIG. 2 illustrates intrinsic Water Use Efficiency (WUE) which is the rate of carbon fixed per unit mole of water transpired. Assimilation rate of carbon (A) is proportional to the difference of intercellular $CO_2$ pressure ($p_i$) and atmospheric $CO_2$ pressure ($p_a$) and the amount of water transpired (E) is driven by the difference between relative humidity within the leaf ($e_i$) and outside the leaf ($e_a$). WUA=A/E. A is represented by the arrow going in to the leaf. E is represented by the arrow going out of the leaf.

Farquhar et al. demonstrated that carbon isotope effect, i.e., the ratio of rate constants for reaction of carbon isotope, $^{12}C$ to $^{13}C$, during photosynthesis correlates with water use efficiency. Intrinsic Water Use Efficiency (WUE) is defined as the rate of carbon fixed per unit mole of water transpired. Farquhar et al., "Stomatal Conductance and Photosynthesis," *Annu. Rev. Plant Physiol.* 33: 317-345 (1982); Farquhar et al., "Carbon Isotope Fractionation and Plant Water-Use Efficiency," *Stable Isot. Ecol. Res.* pp. 21-40 (1986); Farquhara & Richards, "Isotopic Composition of Plant Carbon Correlates with Water-use Efficiency of Wheat Genotypes," *Aust. J. Plant Physiol*, 11(1):539-52 (1984), all of which are hereby incorporated by reference in their entirety. FIG. 2 illustrates intrinsic Water Use Efficiency (WUE) which is the rate of carbon fixed per unit mole of water transpired. Assimilation rate of carbon (A) is proportional to the difference of intercellular $CO_2$ pressure ($p_i$) and atmospheric $CO_2$ pressure ($p_a$) and the amount of water transpired (E).

Both these processes are assumed to be purely diffusive; where assimilation rate of carbon (A) is proportional to the difference of intercellular $CO_2$ pressure ($p_i$) and atmospheric $CO_2$ pressure ($p_a$) and the amount of water transpired (E) is proportional to the leaf-to air vapor pressure difference ($\Delta e = e_i - e_a$). Hence, WUE is defined as:

$$WUE \propto \frac{A}{E} = \frac{g_c(p_a - p_i)}{g_w(e_i - e_a)} = \frac{(p_a - p_i)}{1.6(e_i - e_a)} \qquad \text{Equation 1}$$

Where $g_c$ and $g_w$ are the stomatal conductance for $CO_2$ and water respectively. On accounting for the loss of fixed carbon due to photo-respiration and the carbon uptake by roots, WUE (W) is written as $$W = (1-\varphi)(1-r)\frac{A}{E} = \left(\frac{(1-\varphi)(1-r)p_a(1-p_i/p_a)}{1.6(e_i - e_a)}\right) \qquad \text{Equation 2}$$

$\varphi$: Fraction of photo-respired carbon
$r$: Plant carbon in roots

Based on effect of diffusion and carboxylation of $CO_2$, relationship between discrimination ($\Delta$) and intercellular partial pressures of $CO_2$ using empirical data about rate constants governing both diffusion and carboxylation, is obtained as: $\Delta = (4.4 + 22.6 p_i/p_a) \times 10^{-3}$ Where discrimination is defined as:

$$\Delta = \frac{R_a}{R_p} - 1,$$

where $$R_a = \left(\frac{^{13}C}{^{12}C}\right)_{atmosphere} \quad R_p = \left(\frac{^{13}C}{^{12}C}\right)_{fixed}$$

i.e., molar abundance ratio of $^{13}C$ to $^{12}C$ in atmosphere and that fixed by plants. The definition of water use efficiency and the relation for discrimination, on eliminating $p_i/p_a$, yields:

$$\Delta = \left(27 - \frac{16 \times 22.6}{(1-\varphi)(1-r)p_a}\Delta eW\right) \times 10^{-3} \qquad \text{Equation 3}$$

Water vapor potential ($\Psi$) in leaves is proportional to the difference in chemical potential of water vapor in leaves ($\mu_w$) and in saturated state ($\mu^*_w$):

$$\psi = \frac{\mu_w - \mu^*_w}{\overline{V_w}} = RT\ln(a_w) \qquad \text{Equation 4}$$

and $\overline{V_w}$ is the molar volume of water and $a_w$ is the vapor activity.

The theoretical and experimental development to select breed varieties with higher WUE has largely focused on the isotopic composition of carbon. The theoretical derivation for discrimination considers '$e_i$ as an almost independent parameter' and 'assumes $\Delta e$ is not affected by phenological differences' (Farquhara & Richards, "Isotopic Composition of Plant Carbon Correlates with Water-use Efficiency of Wheat Genotypes," *Aust. J. Plant Physiol.* 11(1):539-52 (1984), which is hereby incorporated by reference in its entirety), while this approximation can be defended for individual leaves, it cannot be defended for an entire canopy, which affects scaling-up the use of $\Delta$ as an indicator of crop performance (Condon et al., "Improving Intrinsic Water Use Efficiency and Crop Yield," *Crop Sci.* 42:122-131 (2002), which is hereby incorporated by reference in its entirety). Measurement of Δ provides no information about the magnitude of A or T or whether the variation is driven by the change in stomatal conductance, photosynthetic capacity or environmental conditions.

The presence of vapor pressure difference in the expression for W implies that W is affected by the environment as well as by the physiological responses of the plant. Wong et al., "Stomatal Conductance Correlates with Photosynthetic Capacity," *Nature* 282:424-426 (1979), which is hereby incorporated by reference in its entirety. Leaf water potential ($\Psi_{leaf}$) represents the best single indicator of plant water status because it integrates environmental conditions (e.g., water availability and evaporative demand), genotype specific plant responses (e.g., stomatal regulation and anatomy) and phenological variation (e.g., leaf position and size). Assessment of leaf water potential still continues to be based on use of pressure chamber measurement or measuring local transpiration rates by controlling local humidity. Relatively narrow distribution in variation of leaf water potential (~95%-100%) adds to challenge of nondestructive accurate measurement. Also, the lack of high-throughput phenotyping methods to measure $\Psi_{leaf}$ on an individual plant basis poses a significant challenge to decoupling the environment and genotype contributions in the assessment of effective water use (EWU) in plants.

The methods and systems described herein are useful for determining the response of a substance (including a plant) to water potential. As will be apparent to the skilled artisan, the dispersible biosensors can be useful in a variety of contexts, including, for example, measuring humidity in micro/nano-environments at a cellular level to assess the biological behavior with environmental parameters; readable output of water content from food products such as fruits and vegetables, which affects the durability and marketability of the products, at individual scale; to measure humidity in microenvironments of porous media (including non-plant media) that are significantly affected by behavior of liquids and salt solutions with relative humidity: such as the damage in building materials due to salt crystallization, humidity induced movement of contaminants in groundwater zone which affects the geochemical and biological activity of groundwater systems; and functionalization of the biosensor with appropriate moieties could be used for multiplexed measurements of property and function at different scales, cellular and meteorological, with change in humidity.

For example, in plants, biosensors may be functionalized with appropriate moieties to detect concentration of abscisic acid or another chemical secreted by plants with change in water potential. A similar response of cells to water potential could be measured by functionalizing biosensors and detecting optical signals in a multiplexed manner. In one embodiment, the contacting and detecting are carried out to measure the humidity of a microenvironment.

In one embodiment, the substance is a plant. In at least one embodiment, the biosensor allows for remote measurement of $\Psi_{leaf}$ at the level of individual plants. The methods and systems described herein can be used for a wide variety of plants or their seeds. The methods and systems described herein for determining a detectable response to change in local water potential (e.g., for in situ sensing of water stress in a plant described below) may, for example, be applied to the leaves, roots, stems, or other parts of the plant. The methods and systems have utility in any kind of agricultural, horticultural, and/or forestry practice. The methods and systems can be used for large scale commercial farming, in open fields or in greenhouse, or even in interiors for decorative plants. Suitable plants include all vascular plants as well as bryophytes (i.e., non-vascular plants). Suitable plants include dicots and monocots. Suitable plants include, for example, crop plants, such as, but not limited to, cereal crops, vegetable crops, fruit crops, flower crops, and grass crops. For example, suitable plants include, but are not limited to, industrial hemp and guayule, as well as agronomic row or other field crops including buckwheat, beans (soybean, snap, dry), corn (grain, seed, sweet corn, silage, popcorn, high oil), cotton, canola, peas (dry, succulent), peanuts, rice, safflower, and sunflower; alfalfa hay and forage crops including alfalfa, clover, vetch, and trefoil; berries and small fruits including blackberries, blueberries, currants, elderberries, gooseberries, huckleberries, loganberries, raspberries, strawberries, and grapes; bulb crops including garlic, leeks, onions, shallots, and ornamental bulbs; citrus fruits including citrus hybrids, grapefruit, kumquat, limes, lemons, oranges, and pummelos; cucurbit vegetables including cucumbers, melons, gourds, pumpkins, squash, and flowers; bedding plants and ornamentals including *Arabidopsis thaliana, Saintpaulia*, petunia, pelargonium, poinsettia, chrysanthemum, carnation, and zinnia; fruiting vegetables including eggplant, sweet and hot peppers, tomatillos, tomatoes, herbs, spices, and mints; hydroponic crops including cucumbers, tomatoes, and lettuce; herbs and spices; leafy vegetables and cole crops including arugula, celery, chervil, endive, fennel, lettuce (head and leaf), parsley, radicchio, rhubarb, spinach, Swiss chard, broccoli, Brussels sprouts, cabbage, cauliflower, collards, kale, kohlrabi, mustard greens, and asparagus; legume vegetable and field crops including snap and dry beans, lentils, succulent and dry peas, peanuts, and soybeans; pome fruit including pears and quince; crops including beets, sugarbeets, red beets, carrots, celeriac, chicory, horseradish, parsnip, radish, rutabaga, salsify, turnips, sugarcane, zucchini, apple, pineapple, and tobacco; shadehouse and other nursery crops including deciduous trees (maple, oak), ornamentals, grapes, citrus, and pine; small grains including barley, rye, wheat, sorghum, and millet; stone fruits including apricots, cherries, nectarines, peaches, plums, and prunes; tree nuts including almonds, beech nuts, Brazil nuts, butternuts, cashews, chestnuts, filberts, hickory nuts, macadamia nuts, pecans, pistachios, and walnuts; tuber crops including potatoes, sweet potatoes, yams, artichoke, cassava, and ginger; and grasses associated with turfgrass, turf, sports fields, parks, established and new preparation of golf course tees, greens, fairways and roughs, seed production and sod production.

In one embodiment, the substance is a building material, such as and without limitation, concrete, ceramics, wood, plaster, paint, metal, stone, plastic, or rubber. In one embodiment, the substance is selected from a foodstuff, building material, soil, synthetic or natural biomaterial, packaging material, and fabric.

In another embodiment, the substance is a packaging material, such as and without limitation, paper or cardboard.

In another embodiment, the substance is a pharmaceutical package, such as and without limitation, a tablet or pill.

In at least one embodiment, the biosensor is non-toxic and biodegradable.

The biosensors according to all aspects of the invention comprise a material capable of giving a detectable response to changes in local water potential. Preferably, the material is one or more nanoparticles/microparticles described herein.

Suitable nanoparticles/microparticles for use in the biosensors of all aspects of the invention include inorganic porous materials (e.g, porous silicon, porous aluminum oxide, porous silica, zeolites, naturally occurring porous minerals, or porous metals). The porous material may, in one embodiment, have pore sizes in the range of about 1-1000 nm. In another embodiment, the pore sizes are in the range of about 30-150 nm. In some embodiments, the pore sizes may be between about 5-150 nm, 10-145 nm, 15-140 nm, 20-135 nm, 25-130 nm, 30-125 nm, 35-120 nm, 40-115 nm, 45-110 nm, and 50-100 nm. In another embodiment, the porous material may have pore sizes larger than 150 nm, including pore sizes up to several hundred nanometers, or 1 micrometer, or even 10 micrometers.

Suitable nanoparticles/microparticles for use in the biosensors of all aspects of the invention also include organic gels (hydrogel).

In at least one embodiment, the nanoparticle/microparticle is a hydrophilic polymer matrix. The hydrophilic polymer matrix of the biosensor of the present invention may, in one embodiment, be formed by polymerization of a first monomer, a second monomer, and a third monomer, wherein the matrix is conjugated with a pair of donor and acceptor fluorophores that exhibit Fluorescence Resonance Energy Transfer. In one embodiment, at least one of the first monomer, second monomer, or third monomer is a cross-linker and at least one of the first monomer, second monomer, or third monomer is a co-monomer.

In one embodiment, the number of polymeric units in the hydrophilic polymer matrix ranges from 10 to 5000, for instance from 20 to 400, for each nanoparticle/microparticle formed from the polymeric units. In another embodiment, the number of polymeric units ranges from 10,000 to 200,000, for instance from 15,000 to 200,000 polymeric units.

The polymer matrix is hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group).

The properties of polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and U.S. Pat. No. 4,946,929; Wang et al., "A Novel Biodegradable Gene Carrier Based on Polyphosphoester," *J. Am. Chem. Soc.* 123:9480 (2001); Lim et al., "Cationic Hyperbranched Poly(amino ester): a Novel Class of DNA Condensing Molecule With Cationic Surface, Biodegradable Three-Dimensional Structure, and Tertiary Amine Groups in the Interior," *J. Am. Chem. Soc.* 123: 2460-1 (2001); Langer, "Biomaterials in Drug Delivery and Tissue Engineering: One Laboratory's Experience," *Acc. Chem. Res.* 33:94-101 (2000); Langer et al., "Selected Advances in Drug Delivery and Tissue Engineering," *J. Control. Release* 62:7-11 (1999); and Uhrich et al., "Polymeric Systems For Controlled Drug Release," *Chem. Rev.* 99:3181-98 (1999), all of which are hereby incorporated by reference in their entirety). More generally, a variety of methods for synthesizing certain suitable polymers are described in The Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., "Facile Synthesis of Block Copolypeptides of Defined Architecture," *Nature* 390:386 (1997); and in U.S. Pat. Nos. 6,506,577, 6,632,922, 6,686,446, and 6,818,732, all of which are hereby incorporated by reference in their entirety.

In some embodiments, the hydrophilic polymer matrix may be modified with one or more moieties and/or functional groups. A variety of moieties or functional groups can be used. In some embodiments, polymers may be modified with polyethylene glycol (PEG), with a carbohydrate, and/or with acyclic polyacetals derived from polysaccharides. Certain embodiments may be made using the general teachings of U.S. Pat. No. 5,543,158 to Gref et al. and WO2009/051837 by Von Andrian et al., both of which are hereby incorporated by reference in their entirety.

In some embodiments, the polymer matrix may be modified with a lipid or fatty acid group. A fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

The polymer matrix may form by copolymerizing (i.e., linking) the first monomer, the second monomer, and the third monomer.

In some embodiments, polymers making up the polymeric matrix are linear or branched polymers. In some embodiments, the polymers can be dendrimers. In some embodiments, the polymers can be substantially cross-linked to one another. In some embodiments, the polymers can be substantially free of cross-links. The matrix of the present invention may also include block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention. In one embodiment of the present invention, the first monomer, second monomer and third monomer are either natural or synthetic or semi-synthetic and together make a hydrophilic cross-linked polymer network.

In at least one embodiment, at least one of the monomers is independently selected from acrylamide or acrylamide derivatives, acrylate or acrylate derivatives, ethylene oxide or its derivatives, ethylene glycol or its derivatives, gelatin, elastin, hyaluronate, cellulose, glycolic acid and its derivatives, lactic acid and its derivatives, caprolactone and its derivatives, trimethylene carbonate and its derivatives, ortho ester and its derivatives, alkyl cyanoacrylate and its derivatives, β-hydroxyalkanoate, and combinations thereof.

In at least one embodiment, at least one of the monomers is an acrylamide monomer. Suitable acrylamide monomers include, but are not limited to, acrylamide, N—N-methylene bisacrylamide, N-3 aminopropyl methacrylamide, N-(tert-butyl) acrylamide, N-(octadecylacrylamide), and (N-diphenylmethyl) acrylamide.

The hydrophilic polymer matrix of the present invention may be formed from one or more polymers, copolymers, or polymer blends. In some embodiments, the one or more polymers, copolymers, or polymer blends are biodegradable. Examples of suitable polymers include poly-acrylamide and hydrophilic organic polymers such as, but not limited to, poly-acrylamide, poly-methylmethacrylate, and poly-hydroxyl-ethylmethacrylate. For example, poly-hydroxyl-ethylmethacrylate could be used as monomer or as block-copolymer such as polyethylene oxide-HEMA. In one embodiment, another monomer with amine, carboxylic acid or thiol end chain may be added to introduce reactive groups for binding onto the monomer and optionally with a corresponding fluorescent dye.

In one embodiment, nano-meter sized polymeric (polyacrylamide) particles may be synthesized by thermally initiated radical polymerization using inverse micro-emulsion in hexane. To regulate the size of particles, ratio of surfactant to water concentration may be selected such that the size distribution of particles is between about 15 nm to about 25 nm. To induce large volume swelling/shrinking response, by for example, a factor of ~10, for gel placed in environment with vapor activity α~95%, concentration of monomer and cross-linker may be appropriately chosen, as suggested by Flory-Rehner theory of hydrogel swelling/shrinking. See, e.g., Flory et al., "Statistical Mechanics of Cross-Linked Polymer Networks II. Swelling," J. Chem. Phys. 11:521-526 (1943), which is hereby incorporated by reference in its entirety.

Techniques for preparing nanoparticles/microparticles are described in literature and known in the art, for example, as described in Clark et al., "Optical Nanosensors for Chemical Analysis Inside Single Living Cells. 1. Fabrication, Characterization, and Methods for Intracellular Delivery of PEBBLE Sensors," Analytical Chemistry 71:4831-4836 (1999) and Clark et al., "Optical Nanosensors for Chemical Analysis Inside Single Living Cells. 2. Sensors for pH and Calcium and the Intracellular Application of PEBBLE Sensors," Analytical Chemistry 71:4837-4843 (1999), both of which are hereby incorporated by reference in their entirety. For example, in one embodiment a polymerization solution may be used that contains monomer such as Acrylamide (AAm), N,N-methylene bisacrylamide (BisAAm), and N-aminorpropyl methacrylamide (APMA) in 100 mM phosphate-buffered saline (PBS) (pH 7.4) buffer. In one embodiment, the weight volume of the monomer may be between 0.01% (w/v) and 25% (w/v). For example, the weight volume of any of the monomers may be between 0.25% (w/v) and 25% (w/v), between 0.3% (w/v) to 5% (w/v). For example, the weight volume of the monomer in one embodiment may be 0.3% (w/v), 0.5% (w/v), and 5% (w/v). In one embodiment, the first monomer is present at a concentration of 3-10% (w/v), a monomer which is a cross-linker is present at a concentration of 0.01-2% (w/v), and a monomer which is co-monomer is present at a concentration of 1-5% (w/v). In one embodiment, the weight volume of the monomer may be between 0.25% (w/v) and 25% (w/v), for example between 0.3% (w/v) to 5% (w/v). For example, the weight volume of the monomer in one embodiment may be 0.3% (w/v), 0.5% (w/v), and 5% (w/v). In one embodiment, the first monomer is present at a concentration of 3-10% (w/v), the monomer which is a cross-linker is present at a concentration of 0.01-2% (w/v), and the monomer which is co-monomer is present at a concentration of 1-5% (w/v).

Concentration of first, second, and third monomers, in particular, a co-monomer, and fluorophores may determine the distance between the fluorophores in the swollen state (relaxed state) of gel at the time of synthesis of nanoparticles and, thereby, the distance between the fluorophore, with the change in the volume of gel.

The solution, in one embodiment, may be sonicated. In one embodiment, hexane is deoxygenated by purging it with nitrogen. deoxygenated hexane, Dioctyl Sulfoccinate Sodium salt (AOT) and Polyoxyethylene(4)lauryl ether (Brij30) may be stirred using magnetic stirrer in a round-bottom flask under nitrogen atmosphere and room temperature, to which polymerization solution may be added. The emulsion may, in one embodiment, be sonicated for a period of time and kept still for a period of time for a microemulsion to form. Ammonium Persulfate (APS) and Tetramethylethylenediamine (TEMED) may be added for initiating free-radical polymerization and the solution may be stirred for a period of time. Once the polymerization is complete, hexane may be removed using rotary evaporation and the particles may be washed using ethanol five times by suspending and precipitating particles using centrifugation.

The dried nanoparticle/microparticle may be resuspended in water and Sodium Borate buffer (pH 8.4) by ultrasonicating it for a period of time. NETS-Ester functionalized Oregon Green 488, for example, and NHS-Rhodamine, for example, may be dissolved in a solvent, for example, anhydrous N,N-Dimethyl formamide (DMF) and then added to the nanoparticle/microparticle solution. The solution may be stirred at room temperature using magnetic stirrer at a particular rpm for a period of time (for example, 4 hours). The conjugated nanoparticle/microparticle may be purified using a kit known in the art against a buffer for a period of several days (for example, 3 days), where the buffer is exchanged several times during the process. Once purified, the nanoparticles/microparticles may be characterized for size, concentration and zeta potential. Methods of making polymeric nanoparticles/microparticles are known in the art, and include solvent evaporation, hot melt particle formation, solvent removal, spray drying, phase inversion, coacervation, and low temperature casting.

For use in plants, biosensor and nanoparticle/microparticle (e.g., hydrophilic polymer matrix) properties can be optimized for response across the range of leaf water potential experienced in typical crop plants (for example, 0 to −2 MPa), and, in coordination with the other descriptions herein, with respect to, for example, dispersal within the mesophyll, signal strength within the leaf, compatibility with direct and proximal detection, minimization of toxicity, and appropriateness of degradation rates.

In one embodiment, the biosensor is biodegradable. In another embodiment, the biosensor is non-toxic.

The biosensor according to the present invention may include a functionalized surface. In one embodiment, the biosensor/nanoparticle/microparticle is negatively functionalized. Alternatively, the biosensor may be positively functionalized. In other embodiments, the biosensor has a no charge or is neutral.

In one embodiment of the present invention, the biosensor/nanoparticle/microparticle may include a releasable cargo that can be located in any place inside or on the surface of the biosensor and/or nanoparticle/microparticle. A trigger for releasing the releasable cargo from the biosensor and/or nanoparticle/microparticle includes, but is not limited to, contact between the biosensor and/or nanoparticle/microparticle and a target plant or substance, or a change of an environmental parameter, such as the pH, ionic condition, temperature, pressure, and other physical or chemical changes, surrounding the biosensor and/or nanoparticle/microparticle.

In one embodiment, the nanoparticle/microparticle (e.g., the hydrophilic polymer matrix) may include a material selected from the group consisting of water, dye molecules, drugs, inorganic ions, organic ions, other water soluble species, metals, and combinations thereof.

In one embodiment, the biosensor may further include at least one stabilizer. The stabilizer may be adsorbed on the surfaces of the nanoparticles/microparticles. The nanoparticles/microparticles may be dispersed into a liquid medium, and the stabilizer may be employed as an adjuvant to aid in the wetting and/or the separation of the individual nanoparticles/microparticles during a dispersion process. The ability of a stabilizer to aid in the wetting and/or the separation of the individual nanoparticles/microparticles may be determined by comparing the dispersion processes for a composition containing the stabilizer and a control composition without the stabilizer. The ability of a stabilizer to aid in the wetting and/or separation of individual nanoparticles/microparticles may be indicated by shorter dispersion times to obtain dispersions of the same average particle diameter, or smaller average particles diameters for the same dispersion time, under similar processing conditions. Alternatively, the stabilizer may be employed to promote stability of the dispersed nanoparticles/microparticles in the liquid medium, preferably an aqueous medium.

The biosensor and/or the nanoparticles/microparticles (e.g., hydrophilic polymer matrix) can have any suitable size. In at least one embodiment, the biosensor and/or nanoparticle is less than about 100 nm in diameter, or less than about 95 nm, less than about 90 nm, less than about 85 nm, less than about 80 nm, less than about 75 nm, less than about 70 nm, less than about 65 nm, less than about 60 nm, less than about 55 nm, less than about 50 nm, less than about 45 nm, less than about 40 nm, less than about 35 nm, less than about 30 nm, less than about 25 nm, less than about 20 nm, less than about 15 nm, less than about 10 nm, less than about 9 nm, less than about 8 nm, less than about 7 nm, less than about 6 nm, less than about 5 nm, less than about 4 nm, less than about 3 nm, less than about 2 nm, or less than about 1 nm. Nanoparticles having a diameter in a range having an upper limit of about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, about 10 nm, about 9 nm, about 8 nm, about 7 nm, about 6 nm, about 5 nm, about 4 nm, about 3 nm, or about 2 nm and a lower limit of about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, about 10 nm, about 9 nm, about 8 nm, about 7 nm, about 6 nm, about 5 nm, about 4 nm, about 3 nm, about 2 nm, or about 1 nm, and any combination thereof, are also contemplated. The present invention further provides that in certain embodiments the biosensor ranges in size from about 50 nm to about 200 nm or from about 10 nm to about 100 nm. In certain embodiments, the size of the biosensor or nanoparticle is about 50 nm to about 150 nm. In other embodiments, the size of the biosensor or nanoparticle can be about 50 nm, about 75 nm, or about 100 nm. In one embodiment, the biosensor comprises multiple nanoparticles. Any of these sizes are also suitable for the biosensor.

In another embodiment, the biosensor or microparticle (e.g., hydrophilic polymer matrix) is as large as several hundred nanometers, 1 micrometer, 2 micrometers, 3 micrometers, 4 micrometers, 5 micrometers, 6 micrometers, 7 micrometers, 8 micrometers, 9 micrometers, or 10 micrometers. For example, the biosensor or microparticle may have a diameter from about 1 μm to about 800 μm. In certain embodiments, the diameter of the microparticle is about 50 to about 500 μm. In other embodiments, the diameter of the microparticle can be about 50 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, or about 800 μm. In another embodiment, the microparticle may be about 1 μm, about 2 μm, about 3 μm, about 4 μm, about 5 μm, about 6 μm, about 7 μm, about 8 μm, about 9 μm, or about 10 μm. In one embodiment, the microparticle has a diameter of about between 1 μm and 20 μm.

The above size ranges apply to both inorganic porous nanoparticles/microparticles and organic nanoparticles/microparticles.

As will be apparent to the skilled artisan, the size selection of the biosensor/nanoparticle/microparticle may depend on whether the biosensor will be used externally or internally. Another consideration is the target response time: larger particles generally respond more slowly to changes in water potential; in external applications, this consideration might set an upper bound on size. Another consideration is the delivery method (e.g., external application, injection, uptake through plant stoma or root, etc.) and the particular architecture/anatomy of the substance for which it will be used. The size may be optimized, for example, to localize at a particular location within the substance (e.g., plant). For example, as will be apparent to the skilled artisan, when the biosensor is used internally in a plant, the size of the biosensor/nanoparticle(s)/microparticle(s) may be selected according to the particular anatomy of the plant. For example, the size may be optimized so that the biosensor/nanoparticle/microparticle can move into the intercellular air space of a plant, as well as enter the apoplastic region of a plant. In a preferred embodiment, the biosensor/nanoparticle(s)/microparticle(s) does not infiltrate the plant cell wall. In at least one embodiment, the biosensor/nanoparticle(s)/microparticle(s) is small enough to infiltrate the stoma but large enough that it does not infiltrate the plant cell wall.

The biosensor or nanoparticle/microparticle can have any suitable shape, for example a mesh, sphere, square, rectangle, triangle, circular disc, cube-like shape, cube, rectangular parallelepiped (cuboid), cone, cylinder, prism, polyhedral, pyramid, right-angled circular cylinder, rod, branched cylindrical, and other regular or irregular shape. In at least one embodiment, the nanoparticle/microparticle is a hydrophilic polymer matrix, e.g., containing entangled and covalently bound polymers. In one embodiment, the hydrophilic polymer matrix is a hydrogel.

Contacting according to all aspects of the invention may be carried out internally, externally, or both. In one embodiment, contacting may involve contacting the exterior of the substance (e.g., plant) to be contacted. For example, in one embodiment, contacting is carried out externally (e.g., on the surface of a plant leaf). In another embodiment, contacting includes contacting internally (e.g., the internal tissues of a plant). For example, in one embodiment, contacting comprises delivering the biosensor to mesophyll (e.g., spongy mesophyll) in a plant leaf. Internal contacting of a plant may be carried out, for example, by delivering the biosensor through the plant stoma or by direct injection. In another embodiment, delivery is carried out through uptake by the roots of a plant, for example by adding the biosensor to irrigation water.

In one embodiment of the present aspect, contacting with the biosensor of the present invention involves contacting with a plurality of biosensors, each of which is capable of dispersing within with the plant or other substance to be contacted.

The biosensors used in the methods herein contain a material that is capable of giving a detectable response to changes in local water potential. In one embodiment, the detectable response is optically detectable. See Vincent et al., "Drying by Cavitation and Poroelastic Relaxations in Porous Media with Macroscopic Pores Connected by Nanoscale Throats," *Physical Review Letters* 113:134501 (2014), which is hereby incorporated by reference in its entirety.

In at least one embodiment, the detectable response is reflectance.

In at least one embodiment, the detectable response is fluorescence. In one embodiment, the fluorescence resonance energy transfer (FRET) is detected, an approach that may provide quality signal-to-noise relative to silicon-based particles. See Lee et al., "Nanoparticle PEBBLE Sensors in Live Cells and in Vivo," *Annual Review of Analytical Chemistry* 2:57-76 (2009), which is hereby incorporated by reference in its entirety. FRET in accordance with the present invention is based on non-radiative transfer of energy (long range dipole-dipole coupling) from a fluorophore acting as donor to another fluorophore acting as acceptor. Examples of acceptor-donor combinations useful in the hydrophilic polymer matrix are (Alexa Fluor 488 and Alexa Fluor 568, $R_O$=6.2 nm), or for the case of postloading the fluorophore (Tetramethyl rhodamine (TMR)) as acceptor in core, and coumarin functionalized shell as the donor. Various other possible acceptor-donor combinations in accordance with the present invention have been reported and are known to those skilled in the art. See, e.g., Sapsford et al., "Materials for Fluorescence Resonance Energy Transfer Analysis: Beyond Traditional Donor-Acceptor Combinations," *Angew. Chemie—Int. Ed.*, 45(28):4562-4588 (2006), which is hereby incorporated by reference in its entirety.

Various fluorescent dyes may be incorporated or post loaded in accordance with the present invention that alter fluorescence based on different phenomena, in response to swelling/shrinking of nanoparticle. For example, in aggregation induced emission/quenching, any fluorescent reporter that exhibits aggregation induced emission (for example Silole based or TPE based), or aggregation induced quenching (for example Fluorescein), could be incorporated in the nanoparticle/microparticle during synthesis whose fluorescence gets modified with increased/decreased configurational space available to the luminogen with swelling/shrinking of nanoparticle. See, e.g., Hong et al., "Aggregation-induced emission," *Chem. Soc. Rev.* 40:5361 (2011) and Zhang et al., "Salt-Responsive Self-Assembly of Luminescent Hydrogel with Intrinsic Gelation-Enhanced Emission," *ACS Appl. Mater. Interfaces* 6:757-762 (2014), both of which are hereby incorporated by reference in their entirety. For in situ measurements, a narrow-band wavelength optical filter may be used to select the excitation light wavelength. The wavelength may, for example, be useful in FRET (e.g., between 470-500 nm or between 470-580 nm) and may be used to excite the biosensor using a reflection probe where optical fibers are used for illumination. The reflected light may, for example, be captured by the central fiber and sent to spectrometer after filtering out the reflected excitation wavelengths, to avoid the saturation of detector, using an emission filter. The spectrometer may, in one embodiment, be connected to a laptop for recording and saving the spectra.

For both a fluorescently detectable or optically detectable response, coupling the degree of hydration of a material may be considered. For rigid porous materials, for example, the wetting and dewetting of the pores is controlled by capillary condensation and drying. In one embodiment, the contacting and detecting are carried out at a cellular level. In one embodiment, the donor and acceptor fluorophores are bound and exhibit aggregation-induced emission. In an alternative embodiment, the donor and acceptor fluorophores are bound and exhibit aggregation-induced quenching.

In at least one embodiment, the biosensor includes nanoparticles/microparticles (e.g., hydrophilic polymer matrix) that are conjugated with a pair of donor and acceptor fluorophores that exhibit Fluorescence Resonance Energy Transfer. Suitable FRET-exhibiting fluorophores used in accordance with all aspects (especially the hydrophilic polymer matrix), may, for example, be selected from the group consisting of xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives.

For example, the fluorophore may be fluorescein, rhodamine, Oregon green, eosin, Texas red, cyanine, indocarbocyanine, oxacarbocyanine, thiacarbocyanine, merocyanine, Seta, SeTau, Square dyes, dansyl derivatives, prodan derivatives, pyridyloxazole, nitrobenzoxadiazole, benzoxadiazole, anthraquinones, including DRAQ5, DRAQ7 and CyTRAK Orange, cascade blue, Nile red, Nile blue, cresyl violet, oxazine 170, proflavin, acridine orange, acridine yellow, auramine, crystal violet, malachite green, porphin, phthalocyanine, and bilirubin. Those skilled in the art will recognize that the dyes listed herein represent an exemplary, not comprehensive, list of dyes that can be of use in accordance with the present invention. In one particular embodiment, at least one of the fluorophores is a xanthene derivative selected from the group consisting of rhodamine, Oregon green, fluorescein, eosin, and Texas red. In one embodiment, at least one or both of the fluorophores have emission in wavelengths of Fraunhofer lines. The fluorophore pairs may exhibit aggregation-induced emission or aggregation-induced quenching.

In one embodiment, the fluorescence of the donor and acceptor fluorophores changes in response to changes in water absorption by the nanoparticle/microparticle (e.g., hydrophilic polymer matrix). In another embodiment, the donor and acceptor fluorophores produce a FRET value that is lower at higher water absorption and higher at lower water absorption.

In one embodiment, if the nanoparticle/microparticle (e.g., hydrophilic polymer matrix) is in a swollen state, there is a relaxed condition, wherein the nanoparticle/microparticle (e.g., hydrophilic polymer matrix) produces a FRET value between the donor fluorophore and acceptor fluorophore that is low compared to when the nanoparticle/microparticle (e.g., hydrophilic polymer matrix) is in a stressed condition. Alternatively, in another embodiment, if the nanoparticle/microparticle (e.g., hydrophilic polymer matrix) is in a collapsed state, there is a stressed condition, wherein the nanoparticle/microparticle (e.g., hydrophilic polymer matrix) produces a FRET value between donor fluorophore and acceptor fluorophore that is high compared to when the nanoparticle is in a relaxed condition.

The biosensor and/or nanoparticle/microparticle (e.g., hydrophilic polymer matrix) can be analyzed by appropriate means. For example, gas chromatographic analysis and high-performance liquid chromatography (HPLC), in particular with a light scattering detector, on a silica column, in the presence of an eluent, e.g., isocratic acetonitrile, may be used. Gas chromatography can also be used.

A second aspect of the present invention relates to a method for in situ sensing of water stress in a plant. The method comprises contacting a plant with a biosensor, where the biosensor comprises a material capable of giving a detectable response to changes in local water potential in the plant and detecting the detectable response thereby sensing water stress in the plant.

Water stress in a plant may occur in a plant when the demand for water exceeds the available amount during a certain period or when poor quality restricts its use. Water stress can occur due to deterioration of fresh water resources in terms of quantity (for example, aquifer over-exploitation, dry rivers, etc.) and/or quality (for example, eutrophication, organic matter pollution, saline intrusion, etc.), and impacts water potential in plants.

Any biosensor described herein is suitable for use in this method. In a preferred embodiment, the biosensor includes a hydrophilic polymer matrix as described herein, Suitable plants include all those described above.

Suitable methods for contacting the plant with the biosensor include any method described herein that is applicable to the delivery of a biosensor to a plant.

Suitable methods for detecting the detectable response include any method described herein.

A third aspect of the present invention relates to a biosensor. The biosensor comprises a hydrophilic polymer matrix as described above, where the matrix is formed by polymerization of a first monomer, a second monomer, and a third monomer, and the matrix is conjugated with a pair of donor and acceptor fluorophores that exhibit Fluorescence Resonance Energy Transfer, as described above.

Any hydrophilic polymer matrix as described above is suitable for use in the biosensor.

A fourth aspect of the present invention relates to a system for determining water potential in a substance. The system comprises an illumination source configured to provide illumination at an excitation wavelength to a substance contacted with a biosensor (e.g., a non-toxic, biodegradable biosensor) comprising a material capable of giving a detectable response to changes in local water potential; a spectrometer configured to receive reflected illumination from the substance and determine an emission spectra based on the detectable response from the material of the biosensor, wherein the spectrometer comprises a hyperspectral imaging device; and a water potential measurement computing device, comprising a processor and a memory coupled to the processor which is configured to execute one or more programmed instructions comprising and stored in the memory to: receive the emission spectra from the spectrometer; receive the emission spectra from the hyperspectral imaging device; and determine a water potential of the substance based on the received emission spectra.

Figure 11:
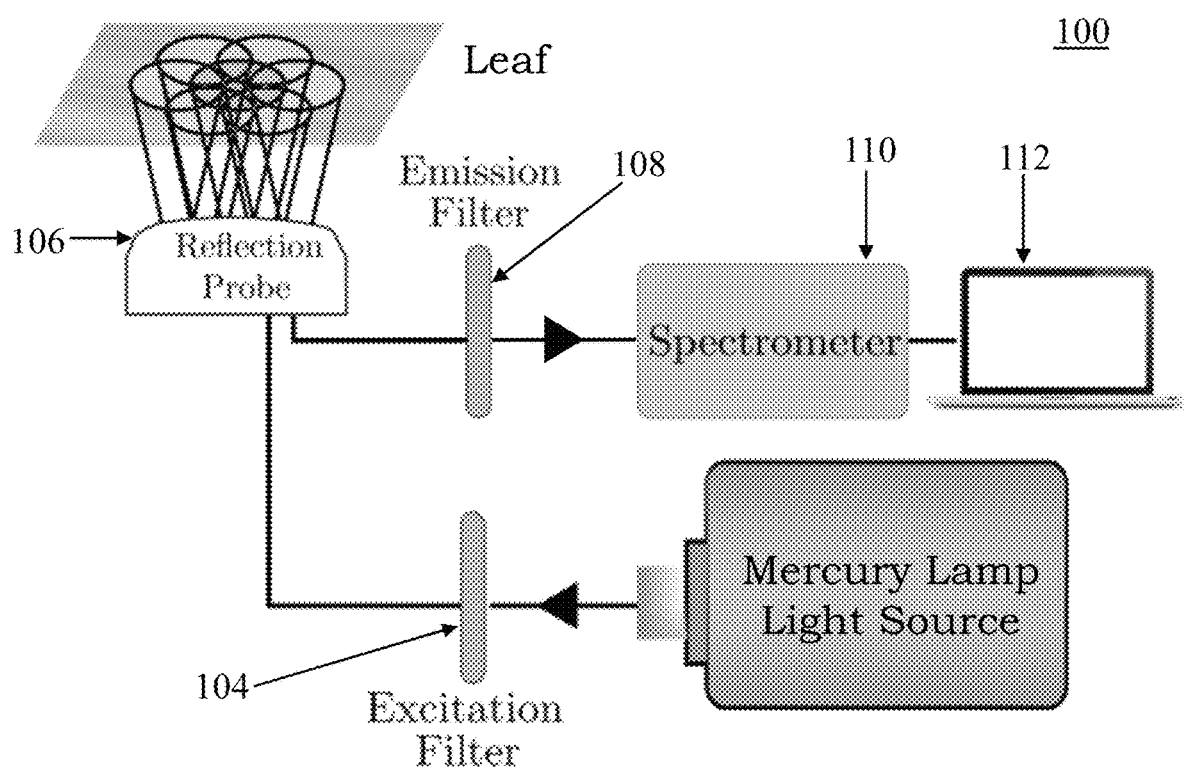
FIG. 11 illustrates an exemplary system (100) for determining water potential in a substance.

FIG. 11 illustrates an exemplary system 100 for determining water potential in a substance. System 100 includes an illumination source 102, an excitation filter 104, a reflection probe 106, an emission filter 108, a spectrometer 110, and a water potential measurement computing device 112, although system 100 may include other types and/or numbers of devices, components, or elements in other combinations, such as, by way of example only, additional optical or electrical devices. System 100 advantageously allows for measuring the water potential of a substance, including for example, in situ sensing of water stress in plants.

Referring again to FIG. 11, illumination source 102 is configured to provide a source of illumination. In this example, illumination source 102 is a mercury lamp, although other illumination sources, such as other types of lamps, lasers, or light emitting diodes may be utilized as illumination source. In one embodiment, the illumination source is a mercury lamp, xenon-arc lamp, halogen-tungsten lamp, laser line, or light-emitting diode (LED). Illumination source 102 is configured to provide the illumination at an excitation wavelength that may be varied depending on the application. In one embodiment, an optical excitation filter optically is coupled to the illumination source and configured to determine the excitation wavelength. In one example, the excitation wavelength is between 470 nm to 500 nm although other excitation wavelengths may be used based on the material being illuminated and excited using illumination source 102. In one embodiment, the optical excitation filter is configured to provide the excitation wavelength between 470 nm and 500 nm.

Excitation filter 104 is optically coupled to illumination source 102 to receive and filter the illumination emitted from illumination source 102. Excitation filter 104 is configured to narrow and determine the excitation wavelength utilized depending on the application. Excitation filter 104 may be any know optical filter in the art. In one embodiment, a reflection probe is configured to provide the illumination from the illumination source to the substance and to collect the reflected illumination from the substance. In one embodiment, the reflection probe comprises a plurality of optical fibers.

Reflection probe 106 is optically coupled to excitation filter 104 to receive illumination passed through excitation filter 104 and provide the illumination, at the excitation wavelength, to a substance for measurement. The substance, such as a leaf by way of example, has been contacted with a non-toxic, biodegradable biosensor comprising a material capable of giving a detectable response to changes in local water potential in accordance with the methods and materials described herein. Reflection probe 106 is positioned to provide the illumination over the surface of the substance. Reflection probe 106 comprises a plurality of optical fibers for receiving and delivering the illumination to the substance. In one example, reflection probe 106 includes at least six optical fibers although other numbers of optical fibers may be employed in reflection probe 106. Reflection probe 106 is also configured to collect reflected illumination from the substance. By way of example, reflection probe 106 may collect the reflected illumination through a central fiber of the plurality of optical fibers.

Emission filter 108 is optically coupled to reflection probe 106 to receive and filter the reflected illumination from the substance collected by reflection probe 106. Emission filter 108 is configured to filter reflected light at the excitation wavelength. Emission filter 108 may be any know optical filter in the art. Emission filter 108 is optically coupled to spectrometer 110 to deliver the filtered reflected light to spectrometer 110. Filtering the excitation wavelength from the reflected light avoids overloading or saturating the detector of spectrometer 110. In one embodiment, an emission filter is optically coupled to the spectrometer to filter reflected illumination at the excitation wavelength prior to the reflected illumination entering the spectrometer. In one embodiment, the system further includes an emission filter to collect illumination from the substance in wavelengths associated with Fraunhofer lines.

Spectrometer 110 is optically coupled to emission filter 108 to receive the reflected from the substance. Spectrometer 110 is configured to determine an emission spectra, such as a fluorescence emission spectra, for the reflected light. In this example, the emission spectra is based on the detectable response from the material of the biosensor utilized as described in further detail herein. Spectrometer 110 may be any spectrometer known in the art. In one embodiment, the method includes determining a FRET efficiency of the received emission spectra; and comparing the FRET efficiency to a calibration curve to determine the water potential of the substance.

Spectrometer 110 is coupled to water potential measurement computing device 112 to provide emission spectra data to water potential computing device 112 for processing.

The present aspect is in accordance with any of the previously described aspects.

A fifth aspect of the present invention relates to a method for determining water potential in a substance. The method comprises receiving, by a water potential measurement computing device, an emission spectra from a spectrometer based on a detectable response from a substance contacted with a biosensor (e.g., a non-toxic, biodegradable biosensor) comprising a material capable of giving the detectable response to changes in local water potential when the substance is illuminated at an excitation wavelength; and determining, by the water potential measurement computing device, a water potential of the substance based on the received emission spectra from the spectrometer.

In one embodiment, the determining the water potential further comprises determining, by the water potential measurement computing device, a FRET efficiency of the received emission spectra; and comparing, by the water potential measurement computing device, the FRET efficiency to a calibration curve to determine the water potential of the sub stance.

The present aspect, particularly the biosensor, is in accordance with any of the previously described aspects.

A sixth aspect of the present invention relates to a water potential measurement computing device. The water potential measurement computing device comprises a processor and a memory coupled to the processor which is configured to execute one or more programmed instructions comprising and stored in the memory to: receive an emission spectrum from a spectrometer based on a detectable response from a substance contacted with a biosensor (e.g., a non-toxic, biodegradable biosensor) comprising a material capable of giving the detectable response to changes in local water potential when the substance is illuminated at an excitation wavelength; and determine a water potential of the substance based on the received emission spectra from the spectrometer.

In one embodiment, the method further includes determining, by the water potential measurement computing device, a FRET efficiency of the received emission spectra; and comparing, by the water potential measurement computing device, the FRET efficiency to a calibration curve to determine the water potential of the substance.

The present aspect, particularly the biosensor, is in accordance with any of the previously described aspects.

A seventh aspect of the present invention relates to a non-transitory computer readable medium having stored thereon instructions for determining water potential in a substance. The non-transitory computer readable medium comprises executable code which when executed by a processor, causes the processor to perform steps comprising: receiving an emission spectra from a spectrometer based on a detectable response from a substance contacted with a biosensor (e.g., a non-toxic, biodegradable biosensor) comprising a material capable of giving the detectable response to changes in local water potential when the substance is illuminated at an excitation wavelength; and determining a water potential of the substance based on the received emission spectra from the spectrometer.

The present aspect, particularly the biosensor, is in accordance with any of the previously described aspects.

Figure 12:
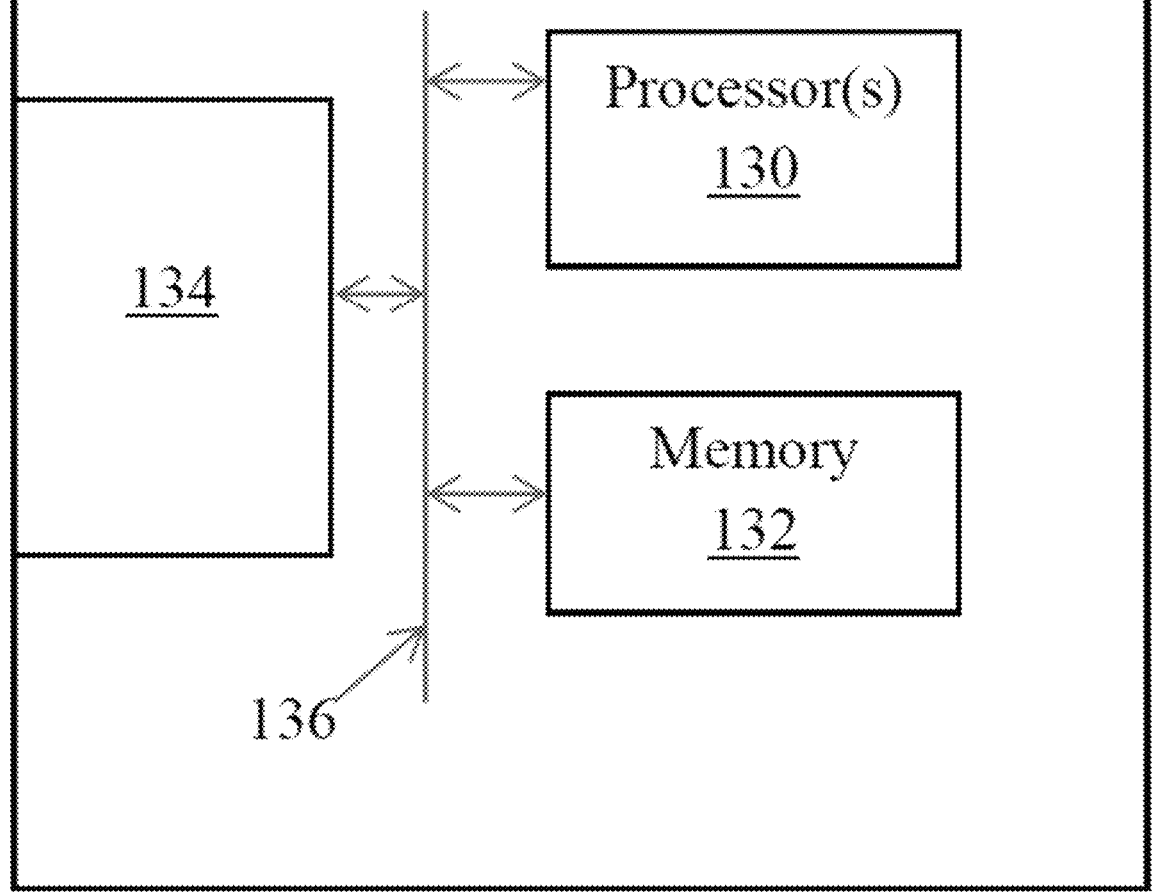
FIG. 12 is a water potential measurement computing device (112).

Referring now more specifically to FIGS. 11 and 12, water potential measurement computing device 112 in this example includes one or more processor(s) 130, a memory 132, and/or a communication interface 134, which are coupled together by a bus 136 or other communication link, although water potential measurement computing device 112 can include other types and/or numbers of elements in other configurations.

Processor(s) 130 of water potential measurement computing device 112 may execute programmed instructions stored in memory 132 for the any number of the functions described and illustrated herein. In one example, processor(s) 130 receive emission spectra from spectrometer 110 and determine a water potential of the substance based on the received emission spectra. Water computing device 112 may average a plurality of spectra in determining the water potential. In one example, the water potential is determined by determining a FRET efficiency of the received emission spectra and comparing the FRET efficiency to a calibration curve as described in more detail in accordance with the methods included herein. Processor(s) 130 may include one or more CPUs, GPUs, or general purpose processors with one or more processing cores, for example, although other types of processor(s) can also be used.

In one embodiment, the method for determining the water potential further includes determining, by the water potential measurement computing device, a FRET efficiency of the received emission spectra; and comparing, by the water potential measurement computing device, the FRET efficiency to a calibration curve to determine the water potential of the sub stance.

Memory 132 stores these programmed instructions for one or more aspects of the present technology as described and illustrated herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s), can be used for the memory 132.

Accordingly, the memory 132 of water potential measurement computing device 112 can store one or more applications or programs that can include computer executable instructions that, when executed by water potential measurement computing device 112, cause water potential measurement computing device 112 to perform actions described and illustrated below with reference to the methods described herein. The application(s) can be implemented as modules, threads, pipes, streams, or components of other applications. Further, the application(s) can be implemented as operating system extensions, module, plugins, or the like. Memory 132 may also be used to store the received emission spectra that may be utilized in adjusting the calibration curve.

Even further, the application(s) may be operative in a cloud-based computing environment. The application(s) can be executed within or as virtual machine(s) or virtual server(s) that may be managed in a cloud-based computing environment. Also, the application(s) may be running in one or more virtual machines (VMs) executing on the image acquisition computing device.

Communication interface 134 operatively couples and communicates between water potential measurement computing device 112 and spectrometer 110 via a communication network, although communication interface 134 may be used to communicate with other devices. Other types and numbers of communication networks or systems with other types and numbers of connections and configurations can be used for communication between water potential measurement computing device 112 and one or more other computing devices, or spectrometer 110. By way of example only, the communications network could use TCP/IP over Ethernet and industry-standard protocols, including NFS, CIFS, SOAP, XML, LDAP, and SNMP. Other types and numbers of communication networks, such as a direct connection, USB, a local area network, a wide area network, modems and phone lines, e-mail, and wireless communication technology, each having their own communications protocols, can be used by the communication networks.

Although the exemplary water potential measurement computing device 112 is described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

In addition, two or more computing systems or devices can be substituted for water potential measurement computing device 112. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only teletraffic in any suitable form (e.g., voice and modem), wireless traffic networks, cellular traffic networks, Packet Data Networks (PDNs), the Internet, intranets, and combinations thereof.

Unless a physical impossibility, any embodiment described herein is combinable with any other embodiment described herein. By way of example, the hydrophilic polymer matrix can have any size and/or shape described herein, in combination with any monomer formulation (including any relative concentration), and any donor/acceptor fluorophore pair described herein.

The examples may also be embodied as one or more non-transitory computer readable media having instructions stored thereon for one or more aspects of the present technology as described and illustrated by way of the examples herein. The instructions in some examples include executable code that, when executed by one or more processors, cause the processors to carry out steps necessary to implement the methods of the examples of this technology that are described and illustrated herein.

EXAMPLES

The following examples are provided to illustrate embodiments of the present invention but they are by no means intended to limit its scope.

Example 1—Synthesis and Physical Characterization of AquaDust Particles

AquaDust (shaded in dark gray) deployed in the mesophyll such that leaf water potential ($\Psi_{leaf}$) can be sensed via calibrated reflectivity or fluorescence (FIG. 1A). Two synthetic approaches to form Ψ-responsive particles that can be loaded through open stomata into the spongy mesophyll are evaluated. The first exploits the tunable wetting and optical properties of porous silicon (FIG. 1B); (Vincent et al., "Drying by Cavitation and Poroelastic Relaxations in Porous Media with Macroscopic Pores Connected by Nanoscale Throats," *Physical Review Letters* 113:134501 (2014), which is hereby incorporated by reference in its entirety) the relative maturity of this approach will allow for the rapid development of aquaDust particles with which to initiate the developments described herein. The second approach exploits the fluorescence resonance energy transfer (FRET) in hydrogels, an approach that has been exploited successfully for a variety of sensing applications (FIG. 1C) and should provide better signal-to-noise relative to silicon-based particles. Lee et al., "Nanoparticle PEBBLE Sensors in Live Cells and in Vivo," *Annual Review of Analytical Chemistry* 2:57-76 (2009), which is hereby incorporated by reference in its entirety. Particle properties will be optimized for response across the range of Ψ experienced in typical crop plants (0 to −2 MPa), and, in coordination with the descriptions below, with respect to dispersal within the mesophyll, signal strength within the leaf, compatibility with direct and proximal detection (FIG. 1D), minimization of toxicity, and appropriateness of degradation rates.

Design considerations. Both formulations that are explored for aquaDust depend on coupling the degree of hydration of a material to an optically measurable response. For rigid porous materials, the wetting and dewetting of the pores is controlled by capillary condensation and drying. The water potential at which this transition occurs is defined by the Young-Laplace equation $$\left(\Psi trans = \frac{2\gamma}{r_{pore}},\right. \quad \text{(Equation 5)}$$

where $\gamma$ [N $m^{-1}$] is the surface tension or water and $r_{pore}$ [m] is the typical pore radius). De Gennes, Pierre-Gilles. *Capillarity and Wetting Phenomena: Drops, Bubbles, Pearls, Waves*. Springer Science and Business (2004), which is hereby incorporated by reference in its entirety. To design particles with a transition in the physiological range of water potential (0 to −2 MPa), particles are formed with $r_{pore}$ in the range from 50 to 500 nm. For hydrogel materials, the swelling transition is controlled by the favorability of the interactions of the polymer backbone with water (Flory Chi parameter, $\chi$[−]) and the shear modulus of the gel, G [Pa]. Flory P. J. *Principles of polymer chemistry*. Cornell University Press (1955), which is hereby incorporated by reference in its entirety. For the target range of water potentials, intermediate values of $\chi$ and a modulus of the order of the target range of water potential (G≡1 MPa) are required. Okay O., in *In Hydrogel sensors and actuators* Springer (2009), which is hereby incorporated by reference in its entirety.

Synthesis—Porous silicon. Building on experience with the synthesis of nanoporous silicon structures (Vincent et al., "Drying by Cavitation and Poroelastic Relaxations in Porous Media with Macroscopic Pores Connected by Nanoscale Throats," *Physical Review Letters* 113:134501 (2014); Pagay et al., "A Microtensiometer Capable of Measuring Water Potentials Below −10 MPa," *Lab on a Chip* 14:2806-2817 (2014); Chen et al., "Stability Limit of Water by Metastable Vapor-Liquid Equilibrium with Nanoporous Silicon Membranes," *Journal of Physical Chemistry B* 120:5209-5222 (2016), all of which are hereby incorporated by reference in their entirety), a route to form silicon-based aquaDust was first developed that will provide Ψ-dependent reflectivity. Briefly, the following was performed: 1) a porous layer was formed on single crystalline silicon wafers (<100> crystallographic orientation) via anodic etching in hydrofluoric acid-ethanol mixtures; 2) this layer was released with a rapid ramp in current; and 3) the porous structure was mechanically crushed into a fine powder of diameter below that of the typical stomatal opening (~20 µm). Taiz, L. *Plant Physiology.* 5th ed, Sinauer Associates (2010), which is hereby incorporated by reference in its entirety. To achieve the desired range of pore sizes, weakly doped, n-type silicon was used ($5\times10^{16}$-$1\times10^{18}$ carriers per $cm^3$) and high current densities (~300 $mA/cm^2$); these conditions will provide pores radii in the range of 30-150 nm with moderate polydispersity. Lehmann et al., "On the Morphology and the Electrochemical Formation Mechanism of Mesoporous Silicon" *Materials Science and Engineering B-Solid State Materials for Advanced Technology* 69:11-22 (2000), which is hereby incorporated by reference in its entirety.

Synthesis—FRET-hydrogels. To form a second class of aquaDust particles with Ψ-dependent fluorescence, the well-understood behavior of gel swelling (Tanaka et al., "Phase Transitions in Ionic Gels," *Physical Review Letters* 45:1636-1639 (1980), which is hereby incorporated by reference in its entirety) was brought together with mature methods of fluorescence resonance energy transfer (FRET) (Sapsford et al., "Materials for Fluorescence Resonance Energy Transfer Analysis: Beyond Traditional Donor—Acceptor Combinations," *Angewandte Chemie International Edition* 45:4562-4589 (2006), which is hereby incorporated by reference in its entirety). Cabodi et al., "Microfluidic Biomaterial," *Journal of the American Chemical Society* 127:13788-13789 (2005); Cabodi et al., An Active Wound Dressing for Controlled Convective Mass Transfer with the Wound Bed," *J. Biomed. Mater. Res*. B 82B:210-222 (2007); Choi et al., "Microfluidic Scaffolds for Tissue Engineering," *Nat. Mater.* 6:908-915 (2007); Wheeler et al., "Transpiration at Negative Pressures in a Synthetic Tree," *Nature* 455:208-212 (2008); Wheeler et al., "Stability Limit of Liquid Water in Metastable Equilibrium with Subsaturated Vapors," *Langmuir* 25:7609-7622 (2009), all of which are hereby incorporated by reference in its entirety. Briefly, sub-micron polyacrylamide particles were formed by thermally initiated radical polymerization in an emulsion in hexanes. Gupta et al., "Multifunctional Nanoplatforms for Fluorescence Imaging and Photodynamic Therapy Developed by Post-Loading Photosensitizer and Fluorophore to Polyacrylamide Nanoparticles," *Nanomedicine: Nanotechnology, Biology and Medicine* 8:941-950 (2012), which is hereby incorporated by reference in its entirety. During synthesis, amine-conjugated comonomers (N-(3-aminopropyl methacrylamide)) were incorporated for covalent coupling of FRET pairs (Lee et al., "Proteolytically Degradable Hydrogels with a Fluorogenic Substrate for Studies of Cellular Proteolytic Activity and Migration," *Biotechnology Progress* 21:1736-1741 (2005), which is hereby incorporated by reference in its entirety), acrylamide monomers to tune the gel's affinity for water (χ), (Tanaka et al., "Phase Transitions in Ionic Gels *Physical Review Letters* 45:1636-1639 (1980), which is hereby incorporated by reference in its entirety) and hydrolysable cross-linkers to control degradation rates. Sawhney et al., "Bioerodible Hydrogels Based on Photopolymerized Poly(Ethylene Glycol)-Co-Poly (.Alpha.-Hydroxy Acid) Diacrylate Macromers," *Macromolecules* 26(4):581-587 (1993), which is hereby incorporated by reference in its entirety. To tune the gels modulus, the monomer and cross-linker concentrations are varied. Wheeler et al., "Stability Limit of Liquid Water in Metastable Equilibrium with Subsaturated Vapors," *Langmuir* 25:7609-7622 (2009), which is hereby incorporated by reference in its entirety. After synthesis, a fluorescent reporter (rhodamine green) with emission (527 nm) was inserted within the open spectral window of chlorophyll (~500 to 600 nm); a non-fluorescent quencher adapted for this emission (BHQ-1 amine) was used. Johansson M. K. in *Fluorescent Energy Transfer Nucleic Acid Probes: Designs and Protocols* ed V. V. Didenko, 17-29, Humana Press (2006), which is hereby incorporated by reference in its entirety.

Physical characterization. Formulations of aquaDust were characterized with respect to hydration state as a function of water potential. Initial characterization was measured with desorption and adsorption isotherms (adsorbed water mass vs. water potential) in air of controlled relative humidity (RH) defined by salt solutions as well as controlling the rate of saturated vapor flow in temperature-controlled vacuum chamber. Vincent et al., "Imbibition Triggered by Capillary Condensation in Nanopores," *Langmuir* 33(7):1655-1661 (2017); Wheeler et al., "Stability Limit of Liquid Water in Metastable Equilibrium with Subsaturated Vapors," *Langmuir* 25:7609-7622 (2009), both of which are hereby incorporated by reference in their entirety. Syntheses were iterated to vary the distribution of pore sizes (silicon) and modulus and χ (hydrogels) to achieve large changes in hydration as Ψ varies between 0 and −2 MPa. Formulations of aquaDust were also characterized with respect to optical and fluorescence response with state of hydration. Initial characterization of optical reflection and FRET response were pursued in the laboratory with microscopes; work in plant leaf material was pursued with optical instruments described below. Formulations of aquaDust were also characterized with respect to kinetics of degradation under environmental conditions. The physical and chemical stability of aquaDust particles in their hydrated state with exposure to light were characterized. The target will be stable responsiveness over a period of 2-3 months to allow for use through an entire growing season with chemical degradation over a period of 1 year to avoid accumulation of these materials in the environment. Degradation rates were controlled by size and porosity (silicon) (Park et al., "Biodegradable Luminescent Porous Silicon Nanoparticles for in Vivo Applications," *Nat Mater* 8:331-336 (2009), which is hereby incorporated by reference in its entirety) and with the concentration of hydrolysable cross-linkers (hydrogel). Sawhney et al., "Bioerodible Hydrogels Based on Photopolymerized Poly(Ethylene Glycol)-Co-Poly (.Alpha.-Hydroxy Acid) Diacrylate Macromers," *Macromolecules* 26(4):581-587 (1993); Hennink et al., "Novel Crosslinking Methods to Design Hydrogels," *Advanced Drug Delivery Reviews* 64:223-236 (2012), both of which are incorporated by reference in their entirety.

Many alternatives exist for each approach: porous aluminum oxide is an alternative to porous silicon that can provide access to larger pore sizes and distinct optical properties and degradation processes (Santos et al., "Nanoporous Anodic Alumina Barcodes: Toward Smart Optical Biosensors," *Advanced Materials* 1050-1054 (2012), which is hereby incorporated by reference in its entirety), a large number of alternative chemistries exist for both the formation of hydrogels (Lee et al., "Nanoparticle PEBBLE Sensors in Live Cells and in Vivo," *Annual Review of Analytical Chemistry* 2:57-76 (2009), which is hereby incorporated by reference in its entirety) and FRET pairs (Sapsford et al., "*Materials for Fluorescence Resonance* Energy Transfer Analysis: Beyond Traditional Donor—Acceptor Combinations," *Angewandte Chemie International Edition* 45:4562-4589 (2006), which is hereby incorporated by reference in its entirety).

Example 2—Methods and Hardware for AquaDust-Based Phenotyping System

Working first with maize, a framework of instruments and methods for data acquisition and analysis was developed to capture time-courses of environmental and plant parameters; once the methods are optimized in maize they will be adapted to wheat. To pursue this project, a leaf measurement system was developed as shown, for example, in FIG. 11. This optical interrogation is compatible with existing systems for measuring chlorophyll fluorescence and transpiration rate (i.e., "Gas Exchange" systems as sold by LiCor). Iterations optimize aquaDust design. Finally, the aquaDust system is integrated with additional measurements of plant and environmental parameters to serve as a basis for phenotyping strategies.

Leaf measurement system for sensing with aquaDust In order to characterize the performance of aquaDust and support new phenotyping strategies, a custom measurement system was developed for use on leaves. At the heart of this system is a spectrometer for visible wavelengths from Ocean Optics (STS Vis spectrometer). This small, lightweight, and relatively inexpensive unit provides appropriate sensitivity and spectral resolution for both reflectance and fluorescence (FRET and chlorophyll) measurements. Initially, a mercury light source (Leica) was used due to its tunable intensity and uniformity across the wavelengths of interest; light emitting diodes will be explored in future iterations to reduce costs and power requirements. Optical fibers were used to couple both the light source and the spectrometer to a spring-loaded clamp that will allow for the creation of well-defined optical paths over the leaf surface (FIG. 1D, FIG. 11). This clamp includes a small gauge thermocouple that will measure the leaf temperature by direct contact. Control and acquisition are handled by custom Oceanview software from a laptop; microcontroller-based interfaces will be worked toward once the methods mature. The use of an emerging commercial platform (MultispeQ) that is being developed as a possible, low-cost tool for use with aquaDust will also be explored in the future. Once these direct methods are optimized, the development of techniques for proximal measurements were initiated with multispectral and thermal imaging instruments. The Ocean Optics spectrometer has shown initial promise as a UAV-deployable tool for reflectance and fluorescence measurements. Burkart et al., "A Novel UAV-Based Ultra-Light Weight Spectrometer for Field Spectroscopy," *IEEE Sensors Journal* 14:62-67 (2014), which is hereby incorporated by reference in its entirety.

Deployment in leaves and in situ characterization of aquaDust Iterating with the synthetic efforts described above, the characteristics of aquaDust particles for use in leaves were optimized. First, methods for the delivery of aquaDust particles to the air-filled spaces in the mesophyll were developed (FIG. 1A). Working with dispersions of particles in water, the following approaches were explored with intact leaves under well-watered conditions with sufficient light to maintain open stomata: painting of dispersion onto both sides of leaf (maize has isobilateral leaves), brief submersion of leaf into dispersion with gentle agitation, and gently pushing dispersion into leaf with a wide-mouthed syringe. In each case, the exterior surfaces of the leaf were thoroughly cleaned after delivery to eliminate external deposits of particles. Next, to define appropriate loading density, microscopy was used to detect the presence of particles in the mesophyll (removal of cuticle maybe necessary), check via gas exchange measurements that stomata remain functional and that $CO_2$ exchange and transpiration are not impeded, and, finally, measure differences in reflectance and fluorescence with the optical system relative to areas of the leaves without particles. Once an appropriate loading strategy is established, the response of aquaDust with $\Psi_{leaf}$ was calibrated with pressure chamber measurements through diurnal cycles of stress and changes in $\Psi_{leaf}$ imposed via the soil by dry-down (FIGS. 7A, 7B) or exposure of roots to solutions of poly(ethylene glycol) of known water potential. Additionally, the optical system and spectral analysis was calibrated for $F_c$ against LiCor gas exchange readings. Finally, multi-week evaluations were made of the stability of the aquaDust signal and of any deterioration of leaf function (loss of turgor, reduced gas exchange, discoloration) in the zones loaded with particles.

This can be used to improve characterizing the plant, create an integrated phenotyping system for diverse genetic mapping populations.

Example 3—Broader Impacts of Research

The development of improved crop varieties sits at the center of national and global priorities to ensure sufficient food for future populations and to enable agriculture to be pursued sustainably. The lack of adequate technologies for phenotyping represents a major bottleneck for this process in general, and for the context of EWU in particular. The new tools and methods developed in this invention will provide transformative advances in the ability to develop crops capable of coping with increasing water scarcity and climate variability. Further, the aquaDust sensing technology may open new routes for the study of water relations in distinct species and contexts, both agricultural and ecophysiological. Finally, the development of methods proposed in the present invention for the use of nanomaterials in plants will lay a foundation for future efforts to monitor and control plant function in situ.

Example 4—Discussion of Motivation

The theoretical and experimental development to select breed varieties with higher WUE (as illustrated in FIG. 2) has largely focused on the isotopic composition of carbon. The theoretical derivation for discrimination considers intercellular vapor pressure, $e_i$, as an almost independent parameter' and 'assumes difference between intercellular and extracellular vapor pressure, $\Delta e$, is not affected by phenological differences' (Farquhara & Richards, "Isotopic Composition of Plant Carbon Correlates with Water-use Efficiency of Wheat Genotypes," *Aust. J. Plant Physiol.* 11(1): 539-52 (1984), which is hereby incorporated by reference in its entirety), while this approximation can be defended for individual leaves, it cannot be defended for an entire canopy, which affects scaling-up the use of carbon isotope discrimination, $\Delta$, as an indicator of crop performance (Condon et al., "Improving Intrinsic Water Use Efficiency and Crop Yield," *Crop Sci.* 42:122-131 (2002), which is hereby incorporated by reference in its entirety). Measurement of A provides no information about the magnitude of A or T or whether the variation is driven by the change in stomatal conductance, photosynthetic capacity or environmental conditions.

The presence of vapor pressure difference in the expression for W implies that W is affected by the environment as well as by the physiological responses of the plant. Wong et al., "Stomatal Conductance Correlates with Photosynthetic Capacity," *Nature* 282:424-426 (1979), which is hereby incorporated by reference in its entirety. Leaf water potential ($\Psi_{leaf}$) represents the best single indicator of plant water status because it integrates environmental conditions (e.g., water availability and evaporative demand), genotype specific plant responses (e.g., stomatal regulation and anatomy) and phenological variation (e.g., leaf position and size). Assessment of leaf water potential still continues to be based on use of pressure chamber measurement or measuring local transpiration rates by controlling local humidity. Relatively narrow distribution in variation of leaf water potential (~95%-100%) adds to challenge of nondestructive accurate measurement. Also, the lack of high-throughput phenotyping methods to measure $\Psi_{leaf}$ on an individual plant basis poses a significant challenge to decoupling the environment and genotype contributions in the assessment of effective water use (EWU) in plants.

The present invention develops a dispersible biosensor that allows for remote measurement of $\Psi_{leaf}$ at the level of individual plants. These dispersible biosensors can be useful in various contexts, including, for example, measuring humidity in micro/nano-environments at cellular level to assess the biological behavior with environmental parameters; readable output of water content from food products such as fruits and vegetables, which affects the durability and marketability of the products, at individual scale; to measure humidity in microenvironments of porous media that are significantly affected by behavior of liquids and salt solutions with relative humidity: such as the damage in building materials due to salt crystallization, humidity induced movement of contaminants in ground-water zone which affects the geochemical and biological activity of groundwater systems; and functionalization of the nanoparticles with appropriate moieties could be used for multiplexed measurements of property and function at different scales, cellular and meteorological, with change in humidity.

Example 5—Particle Infiltration and Fluorescence Readout

As proof-of-concept for fluorescence readout from particles localized at intercellular spaces between upper and lower epidermis of leaf, commercially available fluorescent microspheres were used to infiltrate the leaves using usual agro-infiltration procedure. It was demonstrated that size of particles, concentration of solution, surface functionalization of particles and suspension medium affects the infiltration of particles. For remote readout of fluorescence, sufficiently wide infiltrated zone (~5-6 cm) is achieved.

Figures 3A, 3B:
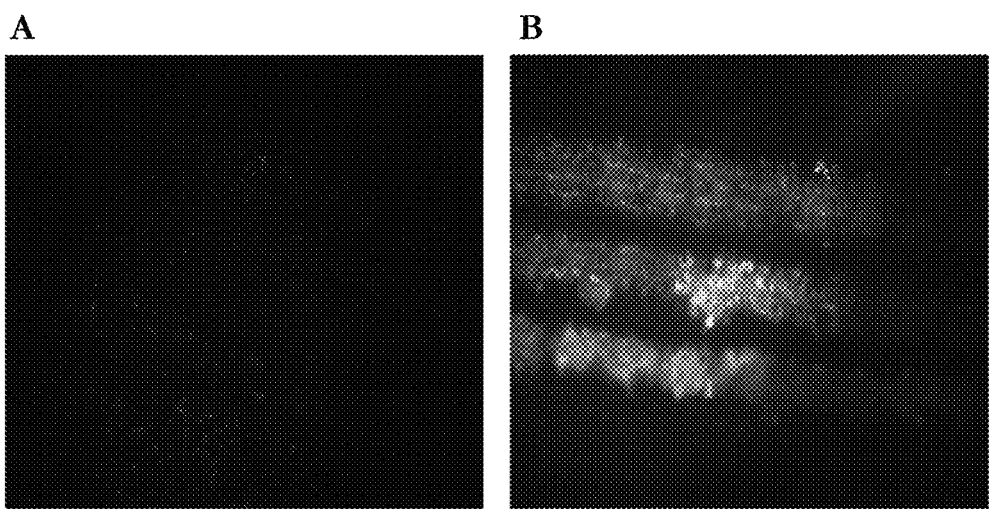
FIGS. 3A-3B show false colored fluorescence images for bead size: 100 nm (FIG. 3A) and 10 nm (FIG. 3B), 3 cm away from the spot of injection in a maize leaf.
Figures 5A, 5B:
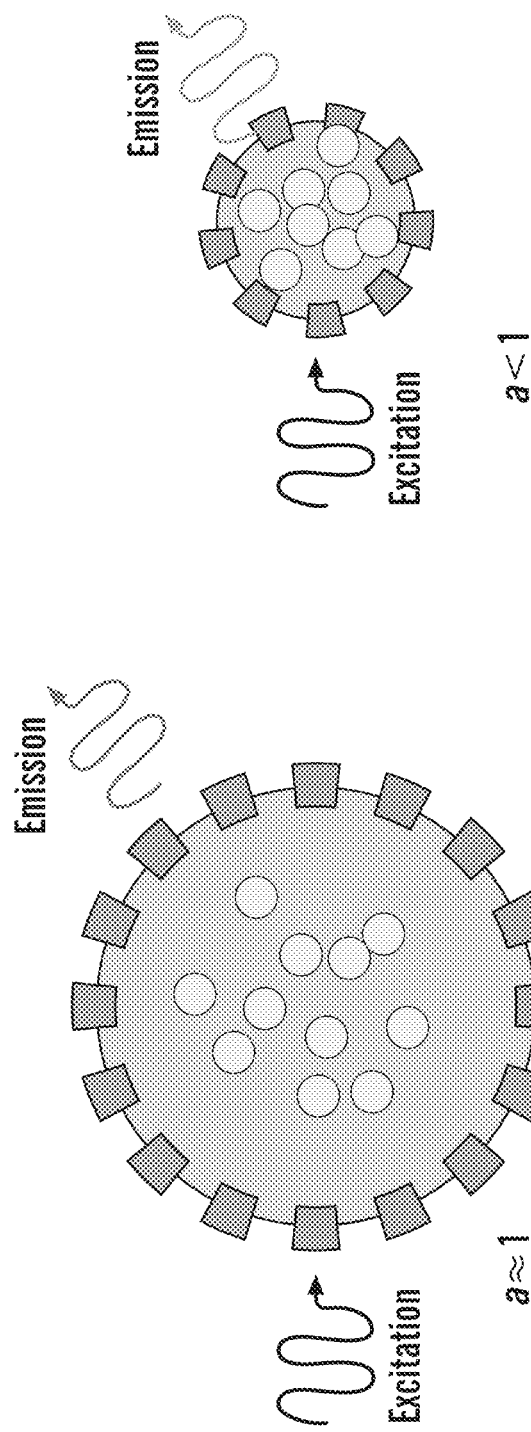
FIGS. 5A-5B depict a sketch of FRET response with donor blue dye (shown by squares) post-loaded on the surface of the polymer matrix (yellow dye (shown by circles) incorporated during synthesis).

Size of particles. The particle size plays a crucial role in getting convectively transported with the solution through mesophyll mesh. In FIGS. 3A-3B, fluorescence is reported for bead size~10 nm and ~100 nm. While fluorescence is observed only very close to the injection spot (<1 cm) for the bead size~100 owing to resistance from mesh of mesophyll cells and vascular bundles, bead size~10 nm infiltrates all the way along with the solution without getting trapped by the mesh. FIGS. 3A-3B show false colored fluorescence images for bead size: 100 nm (FIG. 3A) and 10 nm (FIG. 3B), 3 cm away from spot of injection.

Surface functionalization. Negatively functionalized (—COOH) and neutral particles were used for infiltration and both of these particles showed no difference in infiltration due to surface functionalization, as expected, thereby, suggesting that functionalized nanoparticles could be used for multiplexed measurements.

Suspension Medium. Suspension medium used is 0.01 M IVIES, 0.01 M MgCl2 (pH 5.6). Surfactant was used to demonstrate infiltration without making any damage to epidermis, though, on drying, it led to aggregation of particles. Further trials could be done to explore the effect of surfactant on infiltration.

These results confirm that fluorescent nanoparticles (<20 nm) can be used for remote and high-throughput readout by localizing them in intercellular air space.

Example 6—Synthesis of Hydrogel Nanoparticles

Figure 9:
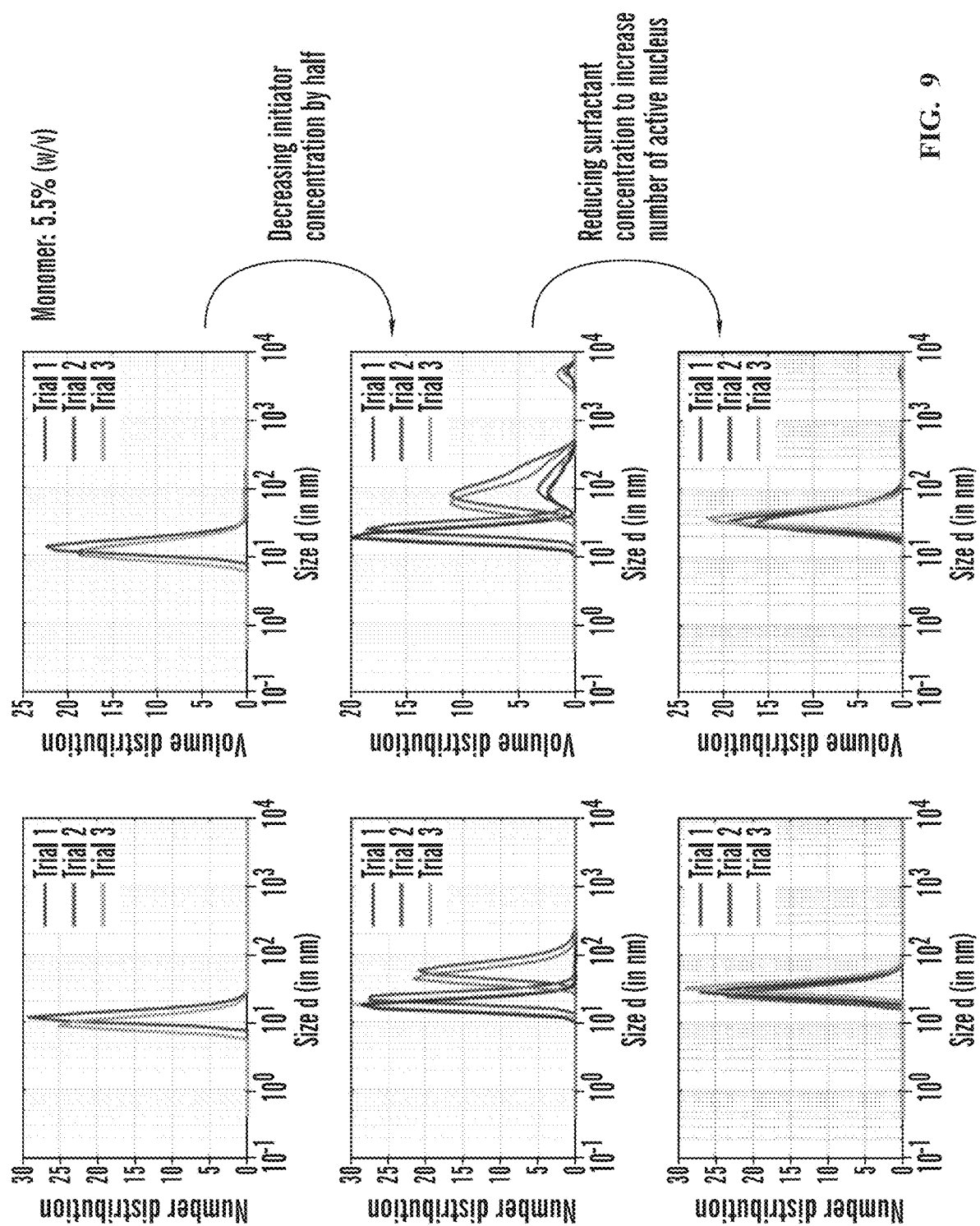
FIG. 9 is a series of graphs that show that nanoparticle size distribution by number and volume can be altered with the change in initiator and surfactant concentration.
Figure 10:
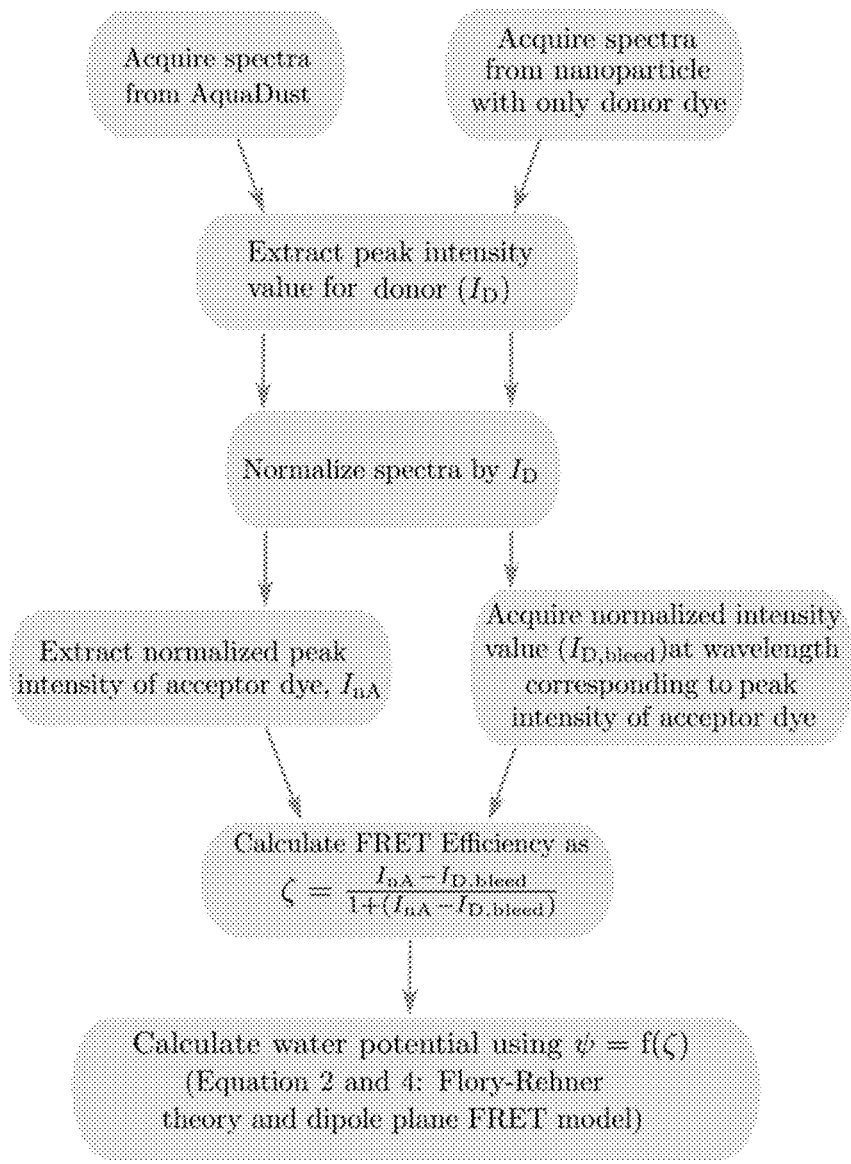
FIG. 10 is a flowchart for spectral analysis.

Nano-meter sized polymeric (poly-acrylamide) particles are synthesized by thermally initiated radical polymerization using inverse micro-emulsion in hexane. To regulate the size of particles, ratio of surfactant to water concentration, initiator concentration and surfactant template is chosen such that the size distribution of particles can be tuned from ~1 to 100 nm. (FIG. 9). Moreno et al., "Production of Singlet Oxygen by Ru(dpp(SO3)2)3 Incorporated in Polyacrylamide PEBBLES," *Sensors Actuators, B Chem.* 90:82-89 (2003); Gao et al., "Nanoparticles for Two-Photon Photodynamic Therapy in Living Cells," *Nano Lett.* 6:2383-2386 (2006); Gao et al., "Ultrafine Hydrogel Nanoparticles: Synthetic Approach and Therapeutic Application in Living Cells," *Angew. Chemie—Int. Ed.* 46:2224-2227 (2007), all of which are hereby incorporated by reference in their entirety.

Figure 8:
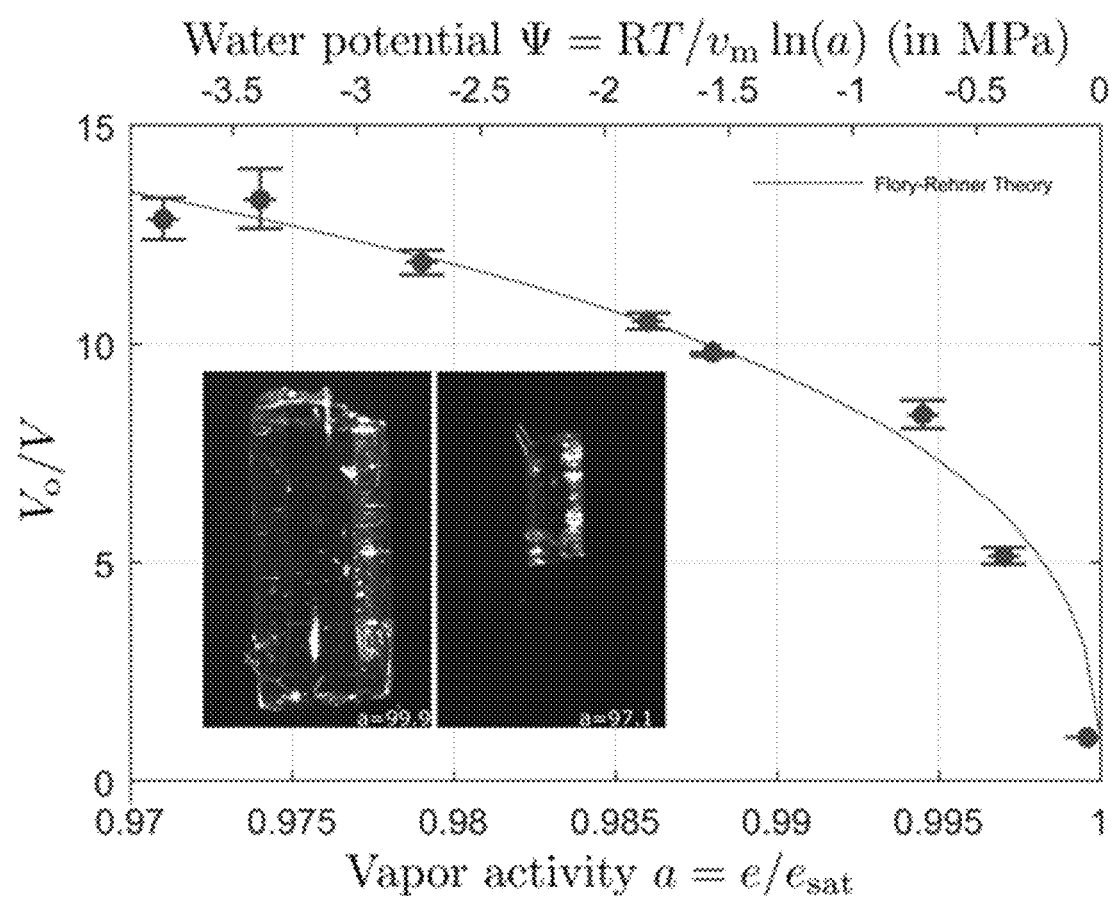
FIG. 8 shows change in volume of bulk gel with change in water potential. $V_o$ is the initial volume of gel and V is the final volume of gel for given vapor activity.

To induce large volume swelling/shrinking response (say, by a factor of >10) for gel placed in environment with vapor activity α~95%, concentration of monomer and cross-linker is appropriately chosen, as suggested by Flory-Rehner theory of hydrogel swelling/shrinking (FIG. 8). Flory et al., "Statistical Mechanics of Cross-Linked Polymer Networks II. Swelling," *J. Chem. Phys.* 11:521-526 (1943), which is hereby incorporated by reference in its entirety. The Flory-Rehner theory of hydrogel swelling/shrinking is based on the phase-equilibria in linear chain polymer solutions as determined by the contribution to the free energy due to polymer/solvent mixing ($\Delta F_{mix}$) and elastic contributions from affine deformation of the network chains from the reference state ($\Delta F_{eias}$):

$$\Delta F = -RT\left(\underbrace{\ln(1-\phi)+\phi+\chi\phi^2}_{\Delta F_{mix}}+\vartheta_o\underbrace{\left[\left(\frac{\phi}{\phi_o}\right)^{1/3}-\frac{\phi}{2\phi_o}\right]}_{\Delta F_{elas}}\right) \quad \text{Equation 6}$$

where R is the gas constant, T is the absolute temperature, $\phi$ is the volume fraction of polymer in gel matrix, $\chi$ is the Flory-Rehner parameter that account for polymer-solvent interaction energy, $\theta_o$ is the effective volume of total cross-link units and serves as important parameter to determine the cross-linker concentration, $=_p$ is the volume fraction of uncross-linked single polymer chain at the time of gelation. For gel to be in equilibrium with osmotic pressure imposed by vapor activity α, i.e., —RT ln α, it could be determined that $\phi$ and $\theta_o$ such that $\phi=\phi_o/\alpha$, where α is the expansion factor. Hino et al., "Swelling Equilibria for Heterogeneous Polyacrylamide Gels," *J. Appl. Polym. Sci* pp. 1635-1640 (1996); Baker, et al., "Effect of Initial Total Monomer Concentration on the Swelling Behavior of Cationic Acrylamide-Based Hydrogels," *Macromolecules* 27:1446-1454 (1994), which are hereby incorporated by reference in their entirety.

Hydrophilic organic polymers such as poly-acrylamide (pAAm) (Gao et al., "Ultrafine Hydrogel Nanoparticles: Synthetic Approach and Therapeutic Application in Living Cells," *Angew. Chemie—Int. Ed.* 46:2224-2227 (2007), which is hereby incorporated by reference in its entirety), poly-methylmethacrylate (pMMA) (Dossi et al., "Synthesis of Fluorescent PMMA-Based Nanoparticles," *Macromol. Mater. Eng* 298:771-778 (2013), which is hereby incorporated by reference in its entirety), poly-hydroxyl-ethylmethacrylate (pHEMA) could be used as monomer or as block-copolymer such as polyethylene oxide-HEMA (pEO-pHEMA) (Oh et al., "Preparation of Nanoparticles of Double-Hydrophilic PEO-PHEMA Block Copolymers by AGET ATRP in Inverse Miniemulsion," *J. Polym. Sci.* 49:487-488 (2008), which is hereby incorporated by reference in its entirety). Another monomer with amine, carboxylic acid or thiol end chain is added to introduce reactive groups for binding onto the monomer as well as the corresponding fluorescent dye.

Example 7—Fluorescence Reporting Strategies

During the synthesis stage of nanoparticles, different fluorescent dyes could be incorporated or post loaded that alter fluorescence based on different phenomena, as outlined, in response to swelling/shrinking of nanoparticle.

Aggregation Induced Emission/Quenching. Any fluorescent reporter that exhibits aggregation induced emission (e.g., Silole based or TPE based) or aggregation induced quenching (e.g., Fluorescein) could be incorporated in the nanoparticle during synthesis whose fluorescence gets modified with increased/decreased configurational space available to the luminogen with swelling/shrinking of nanoparticle. Hong et al., "Aggregation-Induced Emission," *Chem. Soc. Rev.* 40:5361 (2011); Zhang et al., "Salt-Responsive Self-Assembly of Luminescent Hydrogel with Intrinsic Gelation-Enhanced Emission," *ACS Appl. Mater. Interfaces* 6:757-762 (2014), which are hereby incorporated by reference in their entirety.

Fluorescent/Forster Resonance Energy Transfer (FRET). FRET is based on non-radiative transfer of energy (long range dipole-dipole coupling) from fluorophore acting as donor to another acting as acceptor. FRET pairs are chosen such that complete window from FRET efficiency, E=0 to E=1 is attained over the volume change between swollen and shrunk state of gel (FIGS. 4A-4B and 5A-5B); where $$E = \frac{1}{1 + (r/R_o)^6} \quad \text{(Equation 7)}$$

where r is the distance between two fluorophores and $R_O$ is the Forster radius, value known for given acceptor-donor pair. It could be chosen to either incorporate or post-load fluorophore. Gupta & Wang, "Multifunctional Nanoplatforms for Fluorescence Imaging and Photodynamic Therapy Developed by Post-loading Photosensitizer and Fluorophore to Polyacrylamide Nanoparticles," *Nanomedicine* 38(4): 147-153 (2012), which is hereby incorporated by reference in its entirety. Some example of acceptor-donor combinations are (Alexa Fluor 488 and Alexa Fluor 568, $R_O$=6.2 nm), or for the case of post-loading the fluorophore (Tetramethyl rhodamine (TMR) as acceptor in core, coumarin functionalized shell as the donor. Various other possible acceptor-donor combinations have been reported. Sapsford et al., "Materials for fluorescence resonance energy transfer analysis: Beyond traditional donor-acceptor combinations," *Angew. Chemie—Int. Ed.*, 45(28):4562-4588 (2006), which is hereby incorporated by reference in its entirety.

Example 8—Materials and Methods for Fluorescent Nanosensors

Materials. Acrylamide (AAm) (40% (w/v)), N,N-methylene bisacrylamide (BisAAm, >98%), Ammonium Persulfate (APS, >99.99%) were purchased from Sigma-Aldrich, Tetramethylethylenediamine (TEMED, Electrophoresis grade) was purchased from Fisher Scientific. N-aminorpropyl methacrylamide (APMA, >98%) was purchased from Polysciences Inc. Dioctyl Sulfoccinate Sodium salt (AOT, 96%) and Polyoxyethylene(4)lauryl ether (Brij30) was purchased from ACROS Organics, n-Hexane (95%, HPLC Grade) was purchased from Millipore Sigma,N,N-Dimethyl formamide (DMF, Anhydrous) was purchased from Mallinckrodt Inc., Alexa Fluor 488 N-hydroxysuccinimidyl ester (AF488) and Alexa Fluor 568 N-hydroxy succinimidyl ester (AF568) were purchased from Life Technologies, Ethanol (Anhydrous, 100%) and Isopropyl alcohol (IPA) (99%) were purchased from VWR International, Phosphate-buffered saline (PBS) 1x tablet (10 mM Phosphate buffer, 137 mM Sodium Chloride and 2.7 mM Potassium Chloride) was purchased from Amresco.

Nanoparticle Synthesis. Nanoparticles are synthesized using inverse micro-emulsion procedure as Nanoparticle Synthesis described in literature. Clark et al., "Optical Nanosensors for Chemical Analysis Inside Single Living Cells. 1. Fabrication, Characterization, and Methods for Intracellular Delivery of PEBBLE Sensors," *Analytical Chemistry* 71:4831-4836 (1999); Clark et al., "Optical Nanosensors for Chemical Analysis Inside Single Living Cells. 2. Sensors for pH and Calcium and the Intracellular Application of PEBBLE Sensors," *Analytical Chemistry* 71:4837-4843 (1999), both of which are hereby incorporated by reference in their entirety. Briefly, polymerization solution contains 5% (w/v) AAm, 0.3% (w/v) (BisAAm), 0.5% (w/v) APMA in 100 mM phosphate-buffered saline (PBS) (pH 7.4) buffer and is sonicated prior to use. Hexane is deoxygenated by purging it with nitrogen. 4.2 ml of deoxygenated hexane, 0.15 gm AOT and 288 µl Brij30 is stirred using magnetic stirrer in 100 ml round-bottom flask under nitrogen atmosphere and room temperature, to which 200 µl of polymerization solution is added. The emulsion is sonicated for 3 minutes and kept still for next 3 minutes for microemulsion to form. 10 µl APS and 10 µl TEMED is added for initiating free-radical polymerization and the solution is stirred for 2 hours. Once the polymerization is complete, hexane is removed using rotary evaporation and the particles are washed using ethanol five times by suspending and precipitating particles using centrifugation (10000 rpm, 11648 g).

Dye functionalization. 50 mg of dried nanoparticle is resuspended in 1 ml MilliQ water and 5.6 ml 0.1M Sodium Borate buffer (pH 8.4) by ultrasonicating it for 30 minutes. 5 mg of NHS-Ester functionalized Oregon Green 488 and 10 mg of NHS-Rhodamine is dissolved in 200 µl of anhydrous DMF and added to the nanoparticle solution. The solution is stirred at room temperature using magnetic stirrer at 400 rpm for 4 hours. The conjugated nanoparticles are purified using MWCO 10000 Slide-A-Lyzer Dialysis kit against 0.01 M PBS Buffer for 3 days, where the buffer was exchanged six times during the process. Once purified, the nanoparticles were characterized for size, concentration and zeta potential.

Size Characterization. Size and zeta potential of the particles is obtained using Malvern Nano ZS Zetasizer. Particles are resuspended in 100 mM, pH 7.4 PBS buffer using sonication for 40 minutes. Size is measured in 173° backscatter configuration. Concentration was obtained using Malvern Nanosight.

Instrumentation for in-situ measurement in leaves. FIG. 6F shows the sketch of the setup used for in-situ measurement. Briefly, Mercury lamp light source is used as source for illumination, a narrow-band wavelength optical filter is used to select the excitation light wavelength (here, it is 470-500 nm) and is used to excite AquaDust using a reflection probe where six optical fibers are used for illumination. The reflected light is captured by the central fiber and sent to spectrometer after filtering out the reflected excitation wavelengths, to avoid the saturation of detector, using an emission filter. The spectrometer is connected to a laptop for recording and saving the spectra.

Calibration against pressure-chamber. Maize (*Zea mays* L.) inbred line 'B97' was chosen because transpiration rate of 'B97' responses more sensitively to vapor pressure deficit than the majority of the maize nested association mapping founders. Foley R. C., "The Genetic Diversity of Water Use Efficiency in the Nested Associated Mapping Population of *Zea mays*" 9 (2012), which is hereby incorporated by reference in its entirety. A total of 36 maize plants in v4-v5 stages were used in FIGS. 7A-7D experiment with 18 plants under water limited treatment and 18 in well-watered treatment (control). These plants were grown in a greenhouse under a long-day lighting condition (16 h light/8 h dark cycle).

Tip of the leaf is defined as one-third of the total leaf length from the tip end of the leaf (towards the end of the transpiration stream, For leaf 4, the Tip region is approximately 25 cm, while for Leaf 7, the Tip region is about 30 cm). AquaDust is infiltrated in the tip region of the Leaf 4 and Leaf 7 in 3 well-watered and 3 water-limited plants at 10 am on Day 0. Spectra from AquaDust is measured on Day 1 at pre-dawn (5 am-6 am) and mid-day (11 am-2 pm). Pressure chamber measurement is taken from the Tip region of Leaf 4/5 and Leaf 6/7 from all three replicates. Error in the water-potential from pressure chamber is calculated from the values recorded from all three replicates. AquaDust spectra from Leaf 4 is measured from all three replicates and it is compared against the pressure chamber reading; where the pressure chamber measurement from the given plant serves as mean and the error is calculated from the pressure chamber measurement of three replicates.

Depending on the length of the infiltration of aquaDust, a minimum of 3 spectra and a maximum of 6 spectra were recorded from the same infiltration by moving around the optical probe. No distinction has been made in the data collected from the upstream/downstream of the aquaDust infiltration. FRET Efficiency is calculated from the recorded spectra from the normalized peak emission intensity of donor and acceptor dye as shown:

$$\zeta = \frac{x - 0.1148}{1 + (x - 0.1148)} \quad \text{Equation 8}$$

where x is the value of normalized intensity at 580 nm wavelength, 0.1148 is the correction due to the bleed of donor dye emission at 580 nm wavelength. Mean FRET Efficiency is calculated using all the recorded 3/6 spectra.

Response time to step change in water potential. The response time of aquaDust was evaluated for step change in water potential by forcing a transpiring maize leaf to saturation. Briefly, a maize leaf was severed from one side of the midvein. The exposed side is placed in a water-filled Bitran bag (Fisher Scientific Inc.) with the rest of the leaf sticking out of the rubber gasket. The gasket is allowed to seal the chamber and pressurized to 2 bars. The leaf gets saturated instantaneously as water oozes out from the leaf sticking out of the chamber. Spectra measurements are taken and corresponding theoretical water-potential is calculated from the calibration curve.

Example 9—Flory-Rehner Theory for Hydrogel Volume

As discussed above, Flory-Rehner developed the theory of swelling/shrinking of network structures. Flory et al., "Statistical Mechanics of CrossLinked Polymer Networks II. Swelling," *The Journal of Chemical Physics* 11:521-526 (1943), which is hereby incorporated by reference in its entirety. The change in chemical potential of solvent involved in the change of volume of hydrogel, which is in equilibrium with imposed vapor potential, is determined by the contribution to free energy due to entropy and enthalpy of mixing as well as the contribution due to elastic forces of polymer matrix:

$$\Delta\mu = \Psi = -RT\ln(a_s) = \qquad \text{(Equation 9)}$$
$$-RT\left\{\ln(1-\phi) + \phi + \frac{\theta}{2T}\phi^2 + v_w n_o\left[\left(\frac{\phi}{\phi_o}\right)^{1/3} - \frac{\phi}{2\phi_o}\right]\right\}$$

where R=8.314 [J/K] is the universal gas constant, T [K] is the temperature, $\alpha_s$ is the imposed vapor activity, $\varphi$ is the volume fraction of monomer in final state, $\varphi_o$ is the volume fraction of monomer in unpolymerized state, $\theta$ is the flory temperature that accounts for interaction energy between polymer and solvent, $v_w$ is the molar volume of solvent, (in the present case, water) and $n_o$ is the moles of constituent chains per unit volume. The correction was introduced by Tanaka (Tanaka T., "Collapse of Gels and the Critical Endpoint," *Physical Review Letters* 40:820-823 (1978), which is hereby incorporated by reference in its entirety) in the last term on right-hand side of Equation 9 by replacing $\varphi$ with $\varphi/\varphi_o$ that is against the assumption made by Tanaka regarding polymer-solvent interaction at $\varphi_o$=1. For a given gel with known monomer and cross-linker concentration, the change in ratio of volume of gel (=V/V_o≡$\varphi_o$/$\varphi$) where V and $V_o$ are volume of gel in were calculated final state and initial state during gelation respectively.

Distance between fluorophore dyes determines dipole-dipole or dipole-plane interaction between fluorophore molecules. FRET Efficiency, E, in terms of Forster radius ($R_o$), for donor-acceptor stoichiometry being 1:1 ad the distance between fluorophores be given by r, assuming dipole-dipole interaction is given as $$E = \frac{\left(\frac{R_o}{r}\right)^6}{\left(1+\left(\frac{R_o}{r}\right)^6\right)} = \frac{c}{c+\phi^2}, \qquad \text{Equation 10}$$

whereas, for donor-acceptor stoichiometry being 1:1, assuming dipole-plane interaction is given as $$E = \frac{c}{c + \phi^{4/3}}. \quad \text{Equation 11}$$

Example 10—Concentration-Induced Effects on FRET Efficiency

Beer-Lambert Law states that absorbance ($A_{wv}$) for a given wavelength, wv, is a linear function of concentration (c), $$A_{wv} = \log_{10}\frac{I_o}{I} = \epsilon_{wv} lc \quad \text{Equation 12}$$

Where $I_o$ and I are the intensity of the excited light and transmitted light respectively, is the wavelength dependent molar absorptivity coefficient and l is the length of the absorbing sample. The amount of excitation light intensity, i.e., when wavelength wv be ex (for Oregon Green, ex=492 nm), absorbed by the fluorophores, as given by Equation 12:

$$I_{abs,ex} = I_o(1 - 10_{-Aex}) \quad \text{Equation 13}$$

The theoretical fluorescent light intensity, $F_{theo}$, emitted at wavelength, wv and by using Equation 13 to account for the absorbed light intensity, is given by $$F_{theo}(wv) = I_{abs,ex}\varphi E_{wv} \quad \text{Equation 14}$$

where $\varphi$ is the quantum yield efficiency and $E_{wv}$ is the Einstein coefficient of spontaneous emission of transition at wavelength, wv which, in theory, is independent of concentration and should depend only on water potential. On assuming that the emitted light is reabsorbed without re-emission, the observed fluorescence spectra, $F_{obs}$, at any given wavelength, WV, can be corrected using Beer-Lambert's law:

$$F_{obs}(wv) = F_{theo} 10_{Awv} \quad \text{Equation 15}$$

where the absorbance, $A_{wv}$, at any given wavelength, wv as a function of concentration is known. Observed fluorescence intensity, $F_{obs}$, can be written using Equations 13-15, such that $$F_{obs}(wv) = I_o(1 - 10_{-Aex})\varphi E_{wv} 10_{Awv}. \quad \text{Equation 16}$$

Example 11—Physical and Chemical Properties of AquaDust

AquaDust is made of hydrophilic polymer matrix where the monomer (AAm) and cross-linker (BisAAm) concentration dictates its behavior as an 'ideal' gel, whose swelling behavior is well characterized and is underpinned by theoretical model of swelling of non-ionic network structures proposed by Flory-Rehner. Flory et al., "Statistical Mechanics of CrossLinked Polymer Networks II. Swelling," *The Journal of Chemical Physics* 11:521-526 (1943), which is hereby incorporated by reference in its entirety. It was demonstrated that the bulk gel with similar concentration of monomer and cross-linker has swelling behavior as predicted by the theory (FIG. 8).

Figure 6A:
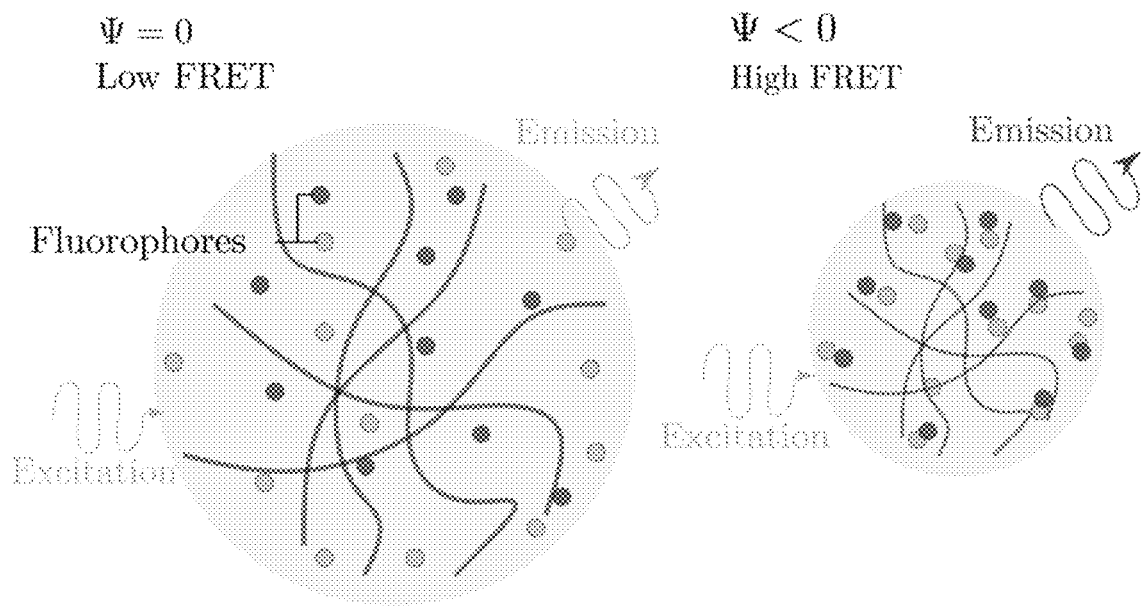
FIGS. 6A-6F show physical and chemical properties of AquaDust and its application in plants.
Figure 6B:
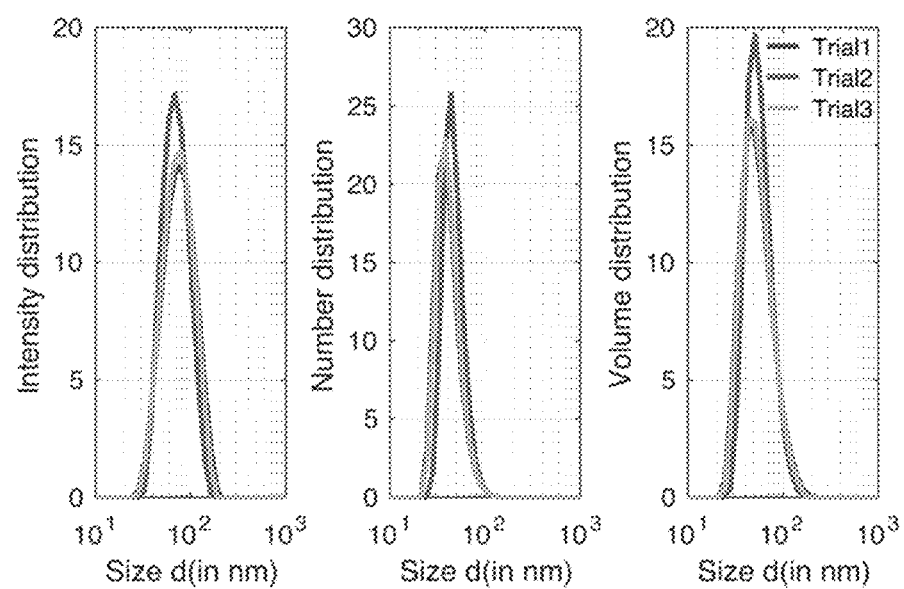
Figure 6C:
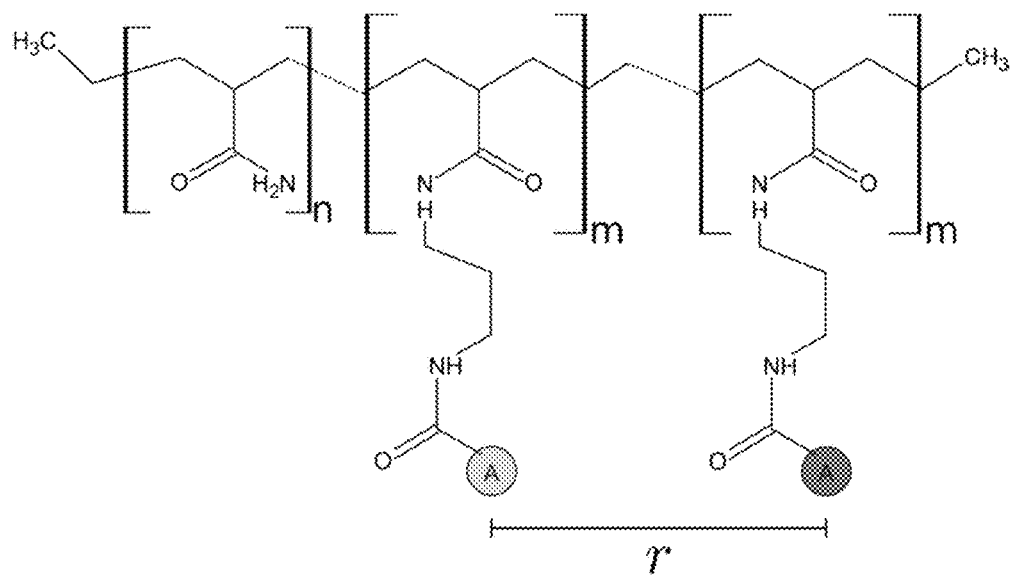

The physical and chemical properties of aquaDust and its application is shown in FIGS. 6A-6E, for example, FIG. 6A shows a schematic of one aquaDust nanoparticle. The size distribution of particles range from 20 nm to 100 nm, and the distribution with respect to intensity, number and volume are consistent as shown in FIG. 6B. Sizes in the order of less than 100 nm allow movement of particles through the apoplast and pattern entire leaf thickness. Initiator, surfactant and water-hexane ratio is optimized to provide unimodal size distribution (Changing concentrations could affect size distribution as shown in FIG. 9).

Figure 6D:
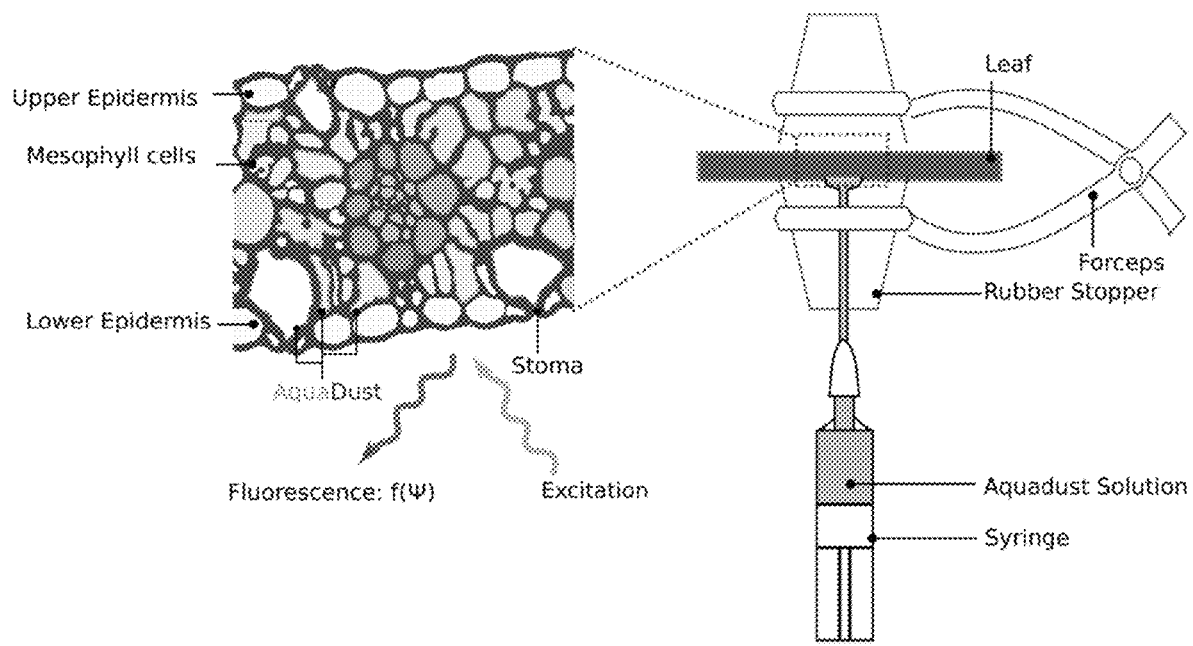
Figure 6E:
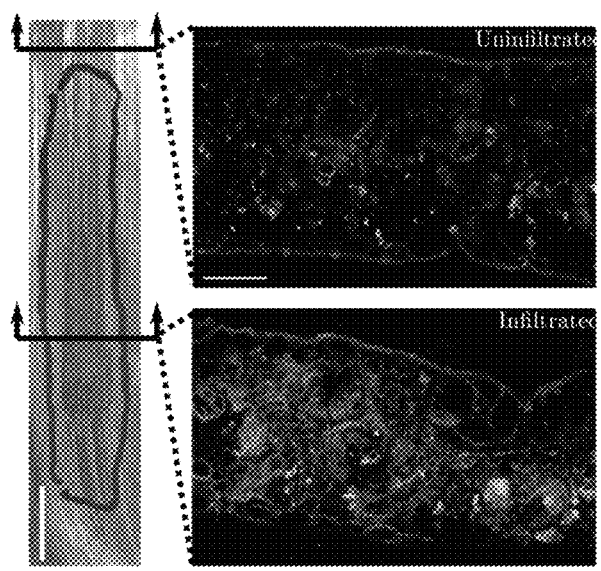
Figure 6F:
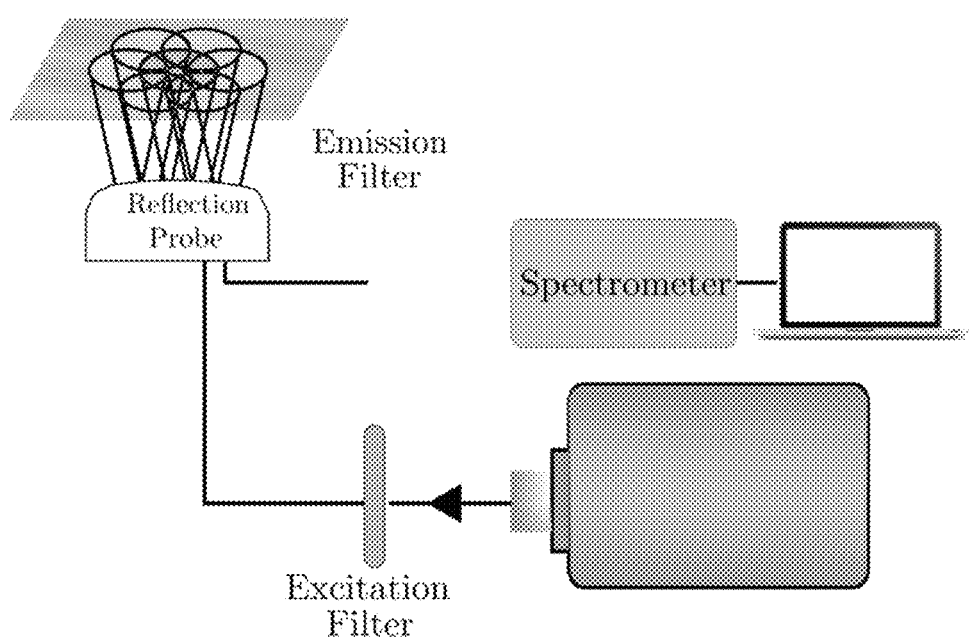

Concentration of co-monomer (APMA) and fluorophores determine the distance between the fluorophores in the swollen state (relaxed state) of gel at the time of synthesis of nanoparticles and, thereby, the distance between the fluorophores, r, (FIG. 6C) with the change in the volume of gel. This concentration regulates the constant 'c' in Equation 10-11 and therefore the resulting FRET Efficiency. Aqua-Dust solution is infiltrated in a leaf using pressure injection of solution by clamping the leaf (FIG. 6D).

Based on the confocal microscope visualization upon infiltration of aquaDust in Maize leaf, it was observed that the AquaDust (emission in channel, see FIG. 6E) disperses throughout the leaf thickness. It is hypothesized that the size distribution of nanoparticles and the hydrophilic surface properties of the nanoparticle allows for the observed dispersion of nanoparticles.

Example 12—Characterization of AquaDust

Based In-situ validation. It was shown that the aquaDust can be used to measure water potential in real-time, nondestructive manner. Validation is done as per the method described above.

Figure 7A:
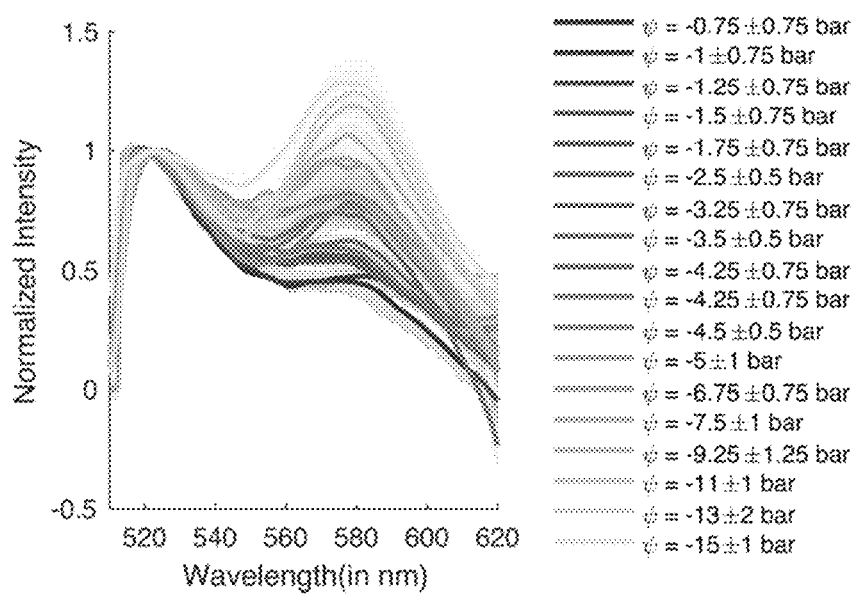
FIGS. 7A-7D depict aquaDust response to water potential.
Figure 7B:
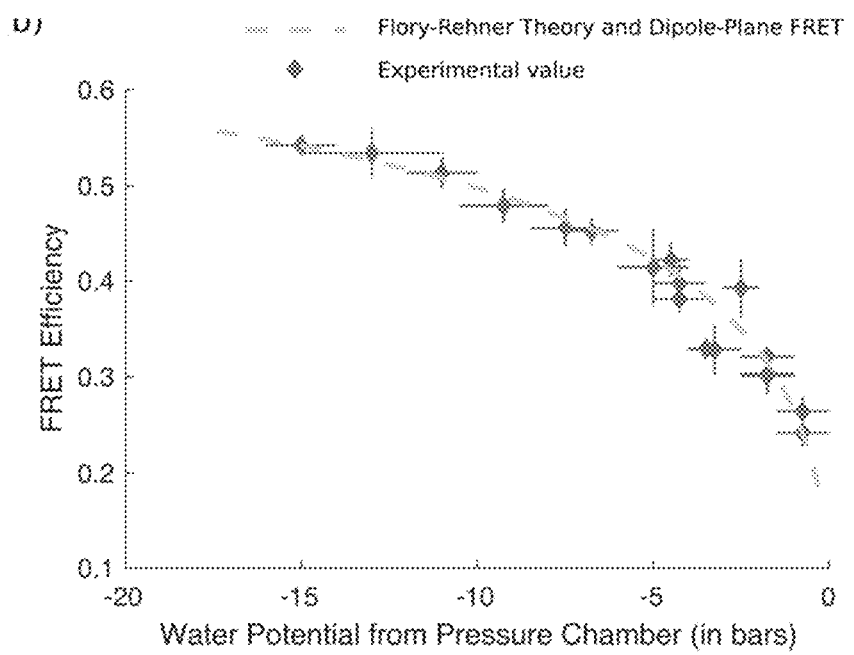
Figure 7C:
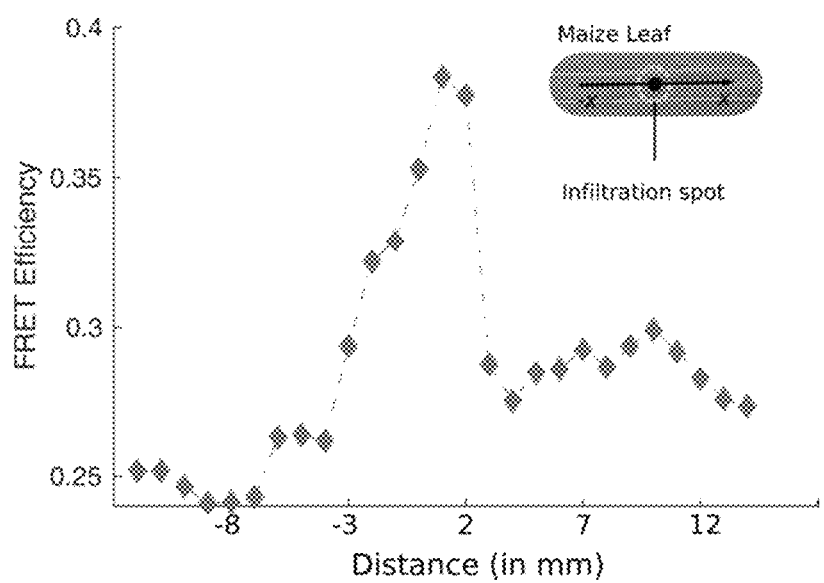
Figure 7D:
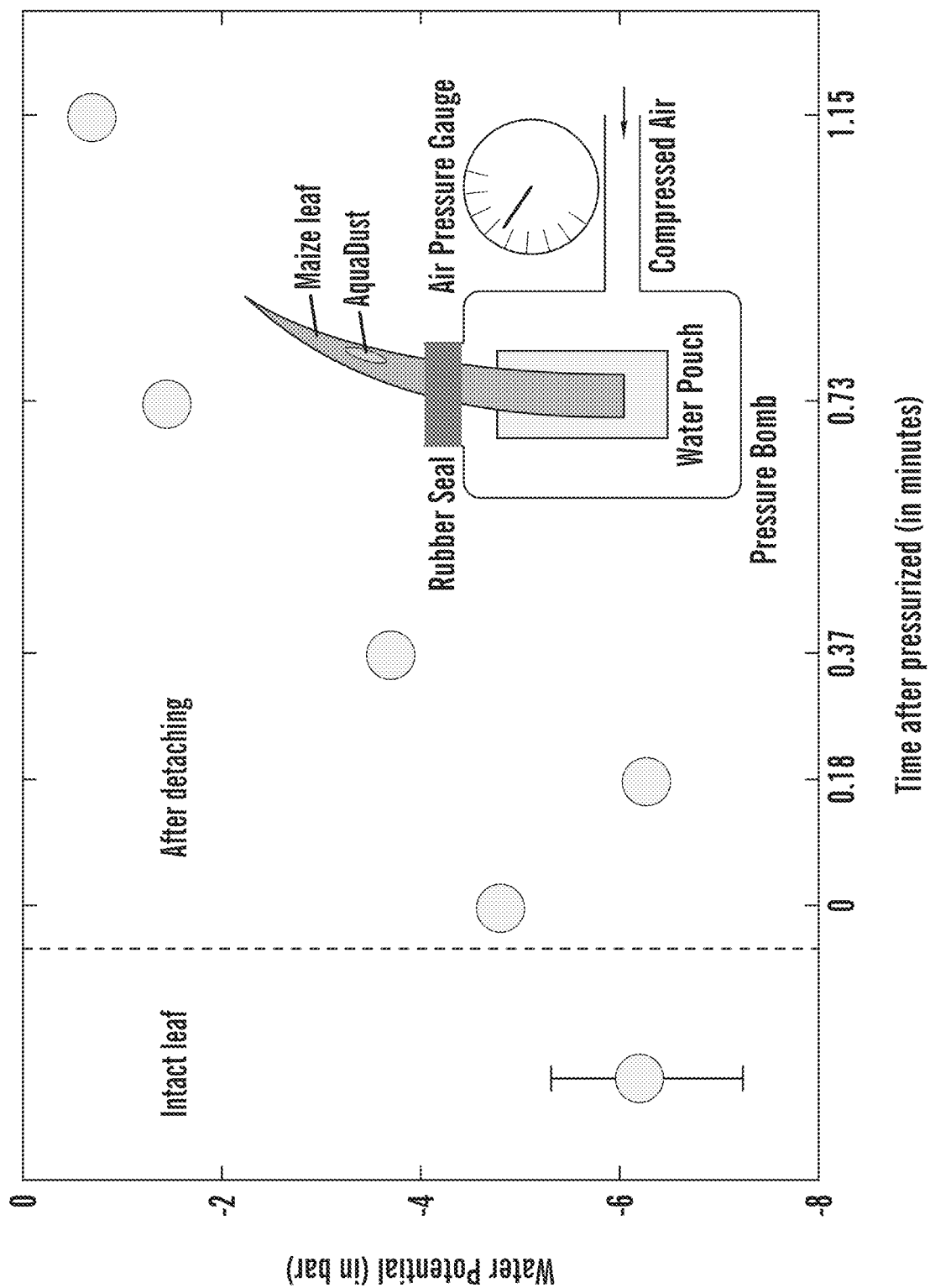

Qualitative increase in emission was observed from the acceptor dye (emission peak wavelength at 580 nm) with decreasing water potential (FIG. 7A). Bold lines represent spectra that are closest to the mean FRET Efficiency obtained for a given water potential. The translucent band represents the error in the spectra as obtained from multiple measurements. FRET Efficiency was extracted from the spectra in FIG. 7A using Equation 8 and is plotted against the water potential (in FIG. 7B). Theoretical prediction as obtained from Flory-Rehner theory and Dipole-Plane FRET model is plotted against water potential measured from the pressure chamber (FIG. 7B). It is observed that experimental values are in excellent agreement with the theoretical prediction. This validates the theoretical model for aquaDust with respect to the change in volume of gel and FRET Efficiency assuming dipole-plane energy transfer.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A biosensor comprising:
   a hydrophilic polymer matrix formed by polymerization of a first monomer, a second monomer, and a third monomer, wherein the matrix is conjugated with a pair of donor and acceptor fluorophores that exhibit Fluorescence Resonance Energy Transfer.

2. The biosensor according to claim 1, wherein the matrix is a nanoparticle of less than about 100 nm in diameter.

3. The biosensor according to claim 1, wherein the matrix is an organic gel.

4. The biosensor according to claim 1, wherein the matrix has a functionalized surface.

5. The biosensor according to claim 4, wherein the matrix is negatively functionalized.

6. The biosensor according to claim 1, wherein at least one of the first monomer, second monomer, or third monomer is a cross-linker and at least one of the first monomer, second monomer, or third monomer is a co-monomer.

7. The biosensor according to claim 6, wherein at least one of the monomers is independently selected from acrylamide or acrylamide derivatives, acrylate or acrylate derivatives, ethylene oxide or its derivatives, ethylene glycol or its derivatives, gelatin, elastin, hyaluronate, cellulose, glycolic acid and its derivatives, lactic acid and its derivatives, caprolactone and its derivatives, trimethylene carbonate and its derivatives, ortho ester and its derivatives, alkyl cyanoacrylate and its derivatives, and β-hydroxyalkanoate.

8. The biosensor according to claim 6, wherein the first monomer is present at a concentration of 3-10% (w/v), the second monomer is a cross-linker present at a concentration of 0.01-2% (w/v), and the third monomer is a co-monomer present at a concentration of 1-5% (w/v).

9. The biosensor according to claim 1, wherein at least one of the monomers is selected from the group consisting of acrylamide, N—N-methylene bisacrylamide, and N-3 aminopropyl methacrylamide, N-(tert-butyl) acrylamide, N-(octadecylacrylamide) and (N-diphenylmethyl) acrylamide.

10. The biosensor according to claim 1, wherein the donor fluorophore and acceptor fluorophore are selected from the group consisting of xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives.

11. The biosensor according to claim 1, wherein at least one of the fluorophores is a xanthene derivative selected from the group consisting of rhodamine, Oregon green, fluorescein, eosin, and Texas red.

12. The biosensor according to claim 1, wherein one or both of the fluorophores have emission in wavelengths of Fraunhofer lines.

13. The biosensor according to claim 1, wherein the monomers are each individually selected from natural monomers, synthetic monomers, and semi-synthetic monomers.

14. The biosensor according to claim 1, wherein the matrix is a hydrogel.

15. The biosensor according to claim 1, wherein the fluorescence of the donor and acceptor fluorophores change in response to changes in water absorption by the matrix.

16. The biosensor according to claim 15, wherein the donor and acceptor fluorophores produce a FRET value that is lower at higher water absorption and higher at lower water absorption.

17. The biosensor according to claim 1, wherein the donor and acceptor fluorophores exhibit aggregation-induced emission.

18. The biosensor according to claim 1, wherein the donor and acceptor fluorophores exhibit aggregation-induced quenching.

19. A method for in situ sensing of water stress in a plant, said method comprising:
contacting a plant with a biosensor according to claim 1, wherein the biosensor comprises a material capable of giving a detectable response to changes in local water potential in the plant, and
detecting the detectable response thereby sensing water stress in the plant.

20. A system for determining water potential in a substance comprising:
an illumination source configured to provide illumination at an excitation wavelength to a substance contacted with a non-toxic, biodegradable biosensor according to claim 1 comprising a material capable of giving a detectable response to changes in local water potential;
a spectrometer configured to receive reflected illumination from the substance and determine an emission spectra based on the detectable response from the material of the biosensor, wherein the spectrometer comprises a hyperspectral imaging device; and
a water potential measurement computing device, comprising a processor and a memory coupled to the processor which is configured to execute one or more programmed instructions comprising and stored in the memory to:
receive the emission spectra from the spectrometer;
receive the emission spectra from the hyperspectral imaging device; and
determine a water potential of the substance based on the received emission spectra.

* * * * *